(12) United States Patent
Goulmy et al.

(10) Patent No.: US 6,878,375 B1
(45) Date of Patent: Apr. 12, 2005

(54) HA-1 ANTIGEN

(75) Inventors: Els A. J. M. Goulmy, Oegstgeest (NL); Donald F. Hunt, Charlottesville, VA (US); Victor H. Engelhard, Charlottesville, VA (US)

(73) Assignee: Rijksuniversiteit te Leiden, Leiden (NL)

( * ) Notice: Subject to any disclaimer, the term of this patent is extended or adjusted under 35 U.S.C. 154(b) by 0 days.

(21) Appl. No.: 09/489,760

(22) Filed: Jan. 21, 2000

Related U.S. Application Data

(63) Continuation of application No. PCT/NL98/00424, filed on Jul. 23, 1998.

(30) Foreign Application Priority Data

Jul. 23, 1997 (EP) .............................................. 97202303

(51) Int. Cl.$^7$ .......................... A61K 39/00; A61K 38/04
(52) U.S. Cl. ................................ 424/185.1; 424/184.1; 530/328
(58) Field of Search ........................... 424/184.1, 185.1; 530/328

(56) References Cited

FOREIGN PATENT DOCUMENTS

| WO | WO 97/05168 | 2/1997 |
|---|---|---|
| WO | WO 97/05169 | 2/1997 |

OTHER PUBLICATIONS

Peakman et al, Immunology 104:361–366, 2001.*
Stryer et al, in Biochemistry, W.H. Freeman and Company, New York, pp. 31–33, 1988.*
Ngo et al, in The Protein Folding Problem and Tertiary Structure Prediction, pp. 492–495, 1994.*
Tisch et al, Proc. Natl. Acad. Sci. USA 91: 437–438, 1994.*
Anderton et al, Immunology 104: 367–76, 2001.*
Colman et al, Effects of amino acid sequence changes on antibody–antigen interaction, 1994, A structural view of immune recognition by antibodies, pp. 33–36.*
Abbas et al, Cellular and Molecular Immunology, 1991, Antigen Presentation and T cell Recognition, p. 130.*
Haan et al, Eur J Immunol 26:2680–2685, 1996.*
Nagase et al, DNA Res 3: 321–329, 1996.*
Paul et al, Fundamental Immunology 2$^{nd}$ edition Raven Press, 1989, pp. 987.*
Goulmy et al., The Role of Human Minor Histocompatibility Antigens in Graft Failure: a Mini–review, Eye, 1995, pp. 180–184, vol. 9, Royal College of Ophthalmologists.
Den Haan et al., Conservation of Minor Histocompatibility Antigens Between Human and Non–human primates, Eur. J. Immunol., 1996, pp. 2680–2685, vol. 26.
Den Haan et al., Identification of a Graft Versus Host Disease–Associated Human Minor Histocompatibility Antigen, Science, Jun. 9, 1995, pp. 1476–1480, vol. 268.
Den Haan et al., The Minor Histocompatibility Antigen HA–1: A Diallelic Gene with a Single Amino Acid Polymorphism, Science, Feb. 13, 1998, pp. 1054–1057, vol. 279.
Van Der Harst et al., Recognition of Minor Histocompatibility Antigens on Lymphocytic and Myeloid Leukemic Cells by Cytotoxic T–Cell Clones, 1994, pp. 1060–1066, The American Society of Hematology.

* cited by examiner

Primary Examiner—Christina Chan
Assistant Examiner—Phuong N Huynh
(74) Attorney, Agent, or Firm—TraskBritt

(57) ABSTRACT

A peptide sequence of the so-called minor H antigen. The minor H antigens are associated with Graft versus Host disease. The peptide and its derivatives find many uses in bone marrow transplantation, organ transplantation, and in the treatment of leukemia. The peptide and its derivatives can be incorporated into vaccines and pharmaceutical formulations, and they can be used in diagnostic test kits. The peptide is derived from the HA-1 minor antigen, and has the sequence VLXDDLLEA (SEQ. I.D. NO. 1), wherein X represents a histidine or arginine residue. Both donors and recipients in bone marrow transplantation can be treated with the peptides, optionally in combination with other peptides, coupled to carriers, and with suitable excipients and/or adjuvants.

6 Claims, 12 Drawing Sheets

HA-1 ANTIGEN

CROSS-REFERENCE TO RELATED APPLICATIONS

This application is a continuation of co-owned International Application No. PCT/NL98/00424, filed on Jul. 23, 1998, designating the United States of America, which itself claims priority from EP 97202303.0 filed on Jul. 23, 1997.

FIELD OF THE INVENTION

The invention relates to the field of immunology, in particular to the field of cellular immunology. Bone marrow transplantation (BMT), one of the areas the invention is concerned with and the area from which the present invention originates, finds its application in the treatment of, for instance, severe aplastic anaemia, leukemia and immune deficiency diseases.

BACKGROUND OF THE INVENTION

In the early days of this technique, many transplants failed because of rejection of the graft by the host. Transplants that did succeed, however, often led to an immune response by lymphocytes present in the graft against various tissues of the host (Graft versus Host Disease "(GvHD)"). It is now known that the GvHD response is mainly due to the presence of major histocompatibility (H) antigens which present a transplantation barrier. Therefore, it is now routine practice to graft only HLA-matched materials (either from siblings or unrelated individuals) resulting in a much improved rate of success in bone marrow transplantation. However, despite this improvement, as well as improvements in pre-transplantation chemotherapy or radiotherapy and the availability of potent immunosuppressive drugs, about 20–70% of the treated patients still suffer from GvHD (the percentage is age and bone marrow donor dependent). To avoid GvHD, it has been suggested to remove the cells (mature T cells) causing the reaction from the graft. This however often leads to graft failure or to recurrence of the original disease. The cells responsible for GvHD are also the cells which often react against the original aberrant cells in, for instance, leukaemia (Graft versus Leukaemia response).

Since BMT is now mainly carried out with HLA matched grafts, the GvHD which still occurs must be caused by another group of antigens. It is very likely that the group of so-called minor H antigens (mHag), which are non-MHC encoded histocompatibility antigens (unlike the major H antigens) are at least partially responsible for the remaining incidence of GvHD. mHag's have originally been discovered in congeneic strains of mice in tumor rejection and skin rejection studies. In mice, the use of inbred strains has shown that mHag are encoded by almost 50 different allelically polymorphic loci scattered throughout the genome. In humans, although cumbersome to identify, mHag have been shown to exist, but their overall number and complexity remains uncertain. Minor H antigens are most likely quite different from each other and quite different from major H antigens, they are probably a diverse and elusive group of fragments of molecules which are participating in various cellular housekeeping functions. Their antigenicity may come very incidentally, as naturally processed fragments of polymorphic proteins that associate with MHC products. Some of the mH antigens appear to be widely expressed on various tissues throughout the body whereas others show limited tissue distribution.

One of the better known minor histocompatibility antigens is the H-Y antigen. H-Y is a mHag that can lead to rejection of HLA-matched male organ and bone marrow grafts by female recipients, and to a higher incidence of GvHD in female-to-male grafts, particularly if the female donor had been previously pregnant. The H-Y antigen may also play a role in spermatogenesis. The human H-Y antigen is an 11 residue peptide derived from SMCY, an evolutionary conserved Y chromosomal protein. Another well known mHag that can lead to GvHD is the HA-2 antigen. The human HA-2 antigen is a 9 residue peptide likely derived from a class I myosin. However, the nature of the HA-1 antigen, responsible for a majority of current cases of GvHD has remained elusive so far. Human bone marrow transplants performed as therapeutical treatment of severe aplastic anaemia, leukaemia and immune deficiency disease became available in the seventies. For the present, the long-term results of allogeneic bone marrow transplantation (BMT) have greatly improved due to the use of HLA-matched siblings as marrow donors, advanced pretransplant chemoradiotherapy, the use of potent immunosuppressive drugs as Graft-versus-Host-Disease (GvHD) prophylaxis, better antibiotics and isolation procedures. Nonetheless, the results of clinical BMT reveal that the selection of MHC identical donors/recipients is not a guarantee of avoidance of GvHD or disease free survival even when donor and recipient are closely related. Allogeneic BMT especially in adults results, depending on the amount of T cell depletion of the graft, in up to 80% of the cases in GvHD. In the HLA genotypically identical situation it amounts to 15–35% whereas in the phenotypical HLA matched recipient/donor combinations, the occurrence of GvHD is significantly higher i.e. 50–80%. Disparities for minor Histocompatibility antigens (mHag) between donor and recipient constitute a potential risk for GvHD or graft failure, which necessitate life long pharmacologic immunosuppression of organ and bone marrow transplant recipient. It is also believed that mHag are involved in the "beneficial" side effect of GvHD i.e. the Graft-versus-Leukemia activity. Several reports demonstrated the presence of anti-host mHag specific CTL in patients suffering from GvHD after HLA genotypically identical BMT. In our laboratory, much effort was put into the further characterization of a (small) number of anti-host mHag specific CTLS. Hereto, CTL clones specific for host mHag were isolated from the peripheral blood (PBL) of patients suffering from severe GvHD. mHag HA-1 specific $CD8^+$ CTL clones were originally obtained after restimulation of in vivo primed PBLs from three patients suffering from GvHD after HLA identical but mHag nonidentical BMT. The post BMT CTL lines were cloned by limiting dilution, resulting in the isolation of a large number of mHag-specific CTL clones. Subsequent immunogenetic analyses revealed that the CTL clones (as described above) identified five non-sexlinked mHag, designated HA-1, -2, -3, -4, -5, which are recognized in a classical MHC restricted fashion. mHag HA-3 is recognized in the presence of HLA-A1 and mHag HA.-1, -2, -4 and 5 require the presence of HLA-A2. Segregation studies demonstrated that each of mHag HA-1 to HA-5 is the product of a single gene segregating in a Mendelian fashion and that HA-1 and HA-2 are not coded within the HLA region. The mHag differ from each other in phenotype frequencies: mHag HA-1 appeared relatively frequent (i.e. 69%) whereas mHag HA-2 appeared very frequent (i.e. 95%) in the HLA-A2 positive healthy population. An inventory in five patients of mHag HA-1, -2, -3, -4 and -5 specific anti-host CTL responses after BMT demonstrated in 3 patients clones specific for the mHag HA-1. This observation points towards the immunodominant behavior of mHag HA-1. With regard to the mHag expressed on different tissues, we observed ubiquitous versus restricted tissue distribution of the mHag analyzed. The expression of the mHag HA-1 is restricted to the cells of the haematopoietic cell lineage, such as thymocytes, peripheral blood lymphocytes, B cells, monocytes. Also, the bone marrow derived professional antigen presenting cells the dendritic cells and the epidermal Langerhans cells, express the mHag HA-1. The mHag HA-1 is also expressed on clonogenic leukemic precursor cells as well as on freshly isolated myeloid and lymphoid leukemic cells, indicating that mHag specific CTLs are capable of HLA class I restricted antigen specific lysis of leukemic cells. To substantiate the importance of the human mH antigenic systems, we investigated whether the mHag are conserved in evolution between human and non human primates. Hereto, cells from non human primates were transfected with the human HLAA2.1 gene. Subsequent analyses with our human allo HLA-A2.1 and four mHag A2.1 restricted CTL clones revealed the presentation of ape and monkey allo and mHag HY, HA-1 and HA-2 peptides in the context of the transfected human HLA-A2.1 molecule by ape and monkey target cells. This implicates that the HA-1 peptide is conserved for at least 35 million years. A prospective study was performed in order to document the effect and clinical relevance of mHag in HLA genotypically identical BMT on the occurrence of acute (grade≧2) GvHD. The results of the mHag typing using the CTL clones specific for five well defined mHag HA-1 to HA-5 demonstrated a significant correlation between mHag HA-1, -2, -4 and -5 mismatch and GvHD. A significant correlation (P=0.024) with the development of GvHD was observed when analyzed for only mHag HA-1. To analyze a putative peptidic nature of the mHag HA-1, we analyzed the requirement of the MHC encoded TAP1 and TAP2 gene products for mHag peptide presentation on the cell surface. The transporter genes TAP1 and TAP2 associated with antigen presentation are required for delivery of peptides from the cytosol with the endoplasmic reticulum. The availability of a human celline "T2" lacking both transport and proteasome subunit genes enabled us to study the processing and presentation of human mHag. We demonstrated that the (rat) transport gene products TAP1 and TAP2u were required for processing and presentation of antigenic peptides from the intracellular mH protein HA-1. Information on the TCR repertoire post BMT in man is extremely scarce. We have analyzed the composition of the T cell receptor (TCR) V region of mHag HA-1 specific CD8+ CTL clones by DNA sequencing of the a and β chains. We observed by analyzing TCR usage of 12 clones derived from 3 unrelated individuals that the TcRβ chains all used the TCRβV6S9 gene segment and showed remarkable similarities within the N-D-N regions.

However, until the present invention no one has succeeded in identifying amino acid sequences of antigenic peptides relevant to the mHag HA-1 antigen, nor has anyone succeeded in the identification of the proteins from which this antigen is derived. We have now for the first time identified a peptide which is a relevant part of mHag HA-1.

DISCLOSURE OF THE INVENTION

Thus this invention provides a (poly)peptide comprising a T-cell epitope obtainable from the minor Histocompatibility antigen HA-1 comprising the sequence VLXDDLLEA (SEQ. I.D. NO. 1) or a derivative thereof having similar functional or immunological properties, wherein X represents a histidine (H) or an arginine (R) residue.

The way these sequences are obtained is described in the experimental part. An important part of this novel method of arriving at the sequences is the purification and the choice of the starting material. The method is therefore also part of the scope of this invention. However, now that the sequence is known, it is of course no longer necessary to follow that method, because the peptides can easily be made synthetically, as is well known in the art. Since routine techniques are available for producing synthetic peptides, it is also within the skill of the art to arrive at analogs or derivatives of the explicitly described peptides, which analogs and/or derivatives may have the same or at least similar functional or immunological properties and or activity. On the other hand analogs which counteract the activity of the explicitly described peptides are also within the skill of the art, given the teaching of the present invention. Therefore, derivatives and/or analogs, be it of the same or different length, be it agonist or antagonist, be it peptide-like or peptidomimetic, are part of the scope of this invention.

The invention provides a (poly) peptide which can be functionally presented to the immune system in the context of the HLA-A2.1 molecule. In general, peptides presented in such a context vary in length from about 7 to about 15 amino acid residues, and a polypeptide can be enzymatically processed to a peptide of such length. A peptide provided by the invention typically is at least 7 amino acids in length but preferably at least 8 or 9 amino acids. The upper length of a peptide provided by the invention is no more than 15 amino acids, but preferably no more than about 13 or 11 amino acids in length. A peptide provided by the invention contains the necessary anchoring residues for presentation in the groove of the HLA-A2.1 molecule. An immunogenic polypeptide provided by the invention comprises a 7–15 amino acid long peptide, provided by the invention, optionally flanked by appropriate enzymatic cleavage sites allowing processing of the polypeptide.

A preferred embodiment of the present invention is the peptide with the sequence VLHDDLLEA (SEQ. I.D. NO. 2) which induces lysis of the cell presenting it at a very low concentration of peptide present. This does not imply that peptides inducing lysis at higher concentrations are not suitable. This will for a large part depend on the application and on other properties of the peptides, which were not all testable within the scope of the present invention. The peptides and other molecules according to the invention find their utility in that they may be used to induce tolerance of the donor immune system in HA-1 negative donors, so that residual peripheral blood lymphocytes in the eventually transplanted organ or the bone marrow, as it may be do not respond to host HA-1 material in a HA-1 positive recipient. In this way GvHD will be prevented or mitigated. On the other hand tolerance can be induced in HA-1 negative recipients in basically the same way, so that upon receipt of an organ or bone marrow from an HA-1 positive donor no rejection on the basis of the HA-1 material occurs. For tolerance induction very small doses can be given repeatedly, for instance intravenously, but other routes of administration may very well be suitable too. Another possibility is the repeated oral administration of high doses of the peptides. The peptides may be given alone, or in combination with other peptides, or as part of larger molecules, or coupled to carrier materials in any suitable excipients. Further applications of the peptide or derivatives thereof lie in the prophylactic administration of such to transplanted individuals to prevent GvHD. This can be done with either agonists, possibly in combination with an adjuvant, or with antagonists which may block the responsible cells. This can be done with or without the concomittant administration of TCR derived peptide sequences or of cytokines. Furthermore the peptides according to the invention can be used to prepare therapeutic agents capable of eliminating a subset of cells, directly or indirectly, especially cells of hematopoietic origin. This can be illustrated by the following examples, which refer to leukemia related therapeutic agents.

A HA-1 positive recipient (in bone marrow transplantation) can be subjected to an additional pre-bone marrow transplant conditioning regime. This means that an agent which specifically recognizes a peptide according to the invention (a HA-1 peptide) as presented selectively on hematopoietic cells, which agent induces elimination of the cells presenting the peptide, is administered to the recipient before transplantation. This agent will eliminate all residual cells (leukemic cells) of hematopoietic origin. Such agents include but are not limited to T cells (which are tailor made ex vivo by pulsing with the peptides provided by the invention, and optionally provided with a suicide gene) and/or antibodies coupled to toxic moieties.

A HA-1 negative donor for bone marrow transplantation can be vaccinated with a peptide according to the invention, a HA-1 peptide. Upon transplantation to a HA-1 positive recipient, the donor's immune system can eliminate any residual or recurrent HA-1 peptide presenting cells in the recipient which are, of course, leukemic. This is another example of tailor-made adoptive immunotherapy provided by the invention. A transplanted HA-1 positive recipient, transplanted with HA-1 negative (or for that matter HA-1 positive) bone marrow and suffering from recurrent disease (relapse), ie. HA-1 positive leukemic cells, can be treated with (again) an agent (as above) which specifically recognizes a peptide according to the invention (a HA-1 peptide) as presented on hematopoietic cells, which agent induces elimination of the cells presenting the peptide. In case of HA-1 positive bone marrow being transplanted to the HA-1 positive recipient, it is still essential (in case of recurrent disease) to eliminate all HA-1 positive cells even though this includes the transplanted material, because otherwise the HA-1positive leukemia will kill the recipient. To avoid the latter case the patient can be re-transplanted, if necessary. In such therapy protocols it is possible to first employ adoptive immunotherapy with agents (cells, antibodies, etc.,) which specifically recognize and eliminate specific peptide expressing cells (e.g. leukemic cells) that need to be destroyed, after which in a second phase the patient is reconstituted with BMT cells replacing the killed cells. The invention thus provides additional (or even substituting) protocols to other therapeutic measures such as radiation.

Other therapeutical applications of the peptide include the induction of tolerance to HA-1 proteins in HA-1 related (auto) immune diseases. On the other hand they may be used in vaccines in HA-1 related (auto) immune diseases.

Diagnostic applications are clearly within the skill of the art. They include, but are not limited to HA-1 typing, detection of genetic aberrances and the like. Specific gene sequences can be detected with various methods known in the art, such as hybridization or amplification with PCR and the like. Immunological detection of peptides has also widely been practiced.

On the basis of the peptide described herein, genetic probes or primers can be produced which can be used to screen for the gene encoding the protein. On the other hand, such probes will be useful in detection kits as well. On the basis of the peptide described herein anti-idiotypic B cells and/or T cells and antibodies are produced. Various techniques, to allow detection of suitable donors or recipients, may be used, based on amplification of HA-1 related nucleic acid sequences or on the immunological detection of HA-1 related peptide sequences. Suitable amplification or detection techniques are known in the art, and the invention enables the production of diagnostic test kits for HA-1 allelic detection and typing. The GvHD associated mHag HA-1 is a peptide derived from one protein allele of a di-allelic genetic system. The identification of this mHag HA-1 enables prospective HA-1 typing of BMT donors and recipients to improve donor selection and thereby prevention of GvHD induction. All these embodiments have been made possible by the present disclosure and therefore are part or the present invention. The techniques to produce these embodiments are all within the skill of the art.

Furthermore, the identification of the HA-1 antigen allows the production of synthetic HA-1 peptides and peptides functionally and/or immunologically related thereto. Such peptides (which can include left or right turning residues) are designed and/or generated by various methods known in the art such as peptide synthesis and replacement mapping, followed by functional binding studies. Altered peptide ligands (APL) for the HLA-A2.1 restricted HA-1 epitope enable modification of the HA-1 directed T cell responses and thus modulate and/or mitigate the GvHD associated T cell response. In general, T cells are activated by the interaction of the T cell receptor (TCR) with the antigenic peptide in the context of a MHC molecule and can react with a number of different effector functions. APL can interact with the TCR and change the effector functions of the T cell qualitatively and/or quantitatively. APL, used in vitro as well as ex vivo can act as antagonist or agonist for the TCR and can anergize the T cells specific for the wild type peptide. The HA-1 peptide is used to induce tolerance in the living bone marrow or organ (kidney, liver, gut, skin, etc.) of HA-1 negative donors for HA-1 positive patients. In bone marrow transplantation, the peptide (given alone or in combination with others) is used to induce tolerance in the living bone marrow donor. The peptide(s) may be given orally, intravenously, intraoccularly, intranasally or otherwise. In all forms of organ, tissue and bone marrow transplantation, the HA-1 peptide is used to induce tolerance in HA-1 negative recipients.

The invention also provides an analog of the peptide according to the invention which is an antagonist for the activity of T cells recognizing the peptide. Such an analog is obtained using methods and tests known in the art. Furthermore, the invention provides a method for the generation of antibodies, T cell receptors, anti-idiotypic B-cells or T-cells, comprising the step of immunization of a mammal with a peptide or a polypeptide according to the invention, and the antibodies, T-cell receptors, B-cells or T-cells obtainable by the method. Dose ranges of peptides and antibodies and/or other molecules according to the invention to be used in the therapeutical applications as described herein before are designed on the basis of rising dose studies in the clinic in clinical trials for which rigorous protocol requirements exist.

An important advantage of using .mHag-specific CTLs in adoptive immunio therapy of for example leukemia lies in their restricted and specific target cell damage. We take advantage of three of the known characteristics of human mHag ie. 1) MHC-restricted recognition by T cells; 2) variable phenotype frequencies, i.e.—mHag polymorphism; and 3) restricted tissue distribution, allowing specific and distinct targeting of mHag HA-1 related therapy. Restrictive HA-1 tissue expression significantly increases the success of adoptive immunio therapy towards various types of cancer, such as small cell lung carcinoma cells which express also the HA-1 antigen. Moreover, since mHag are clearly expressed on circulating leukemic cells and clonogenic leukemic precursor cells of both myeloid and lymphoid origin, both types of leukemias can be targeted. mHag peptide CTLs can be generated exvivo from mHag-negative BM donors for mHag-positive patients. Peptide-specific CTL clones from an HLA-A1-positive mHag-negative healthy blood donor are generated by pulsing autologous APCs with mHag HA-1 related synthetic peptide. Proliferating clones are expanded and tested for specific cytotoxic activity. Upon transfusion (either pre-BMT as part of the conditioning regimen or post-BMT as adjuvant therapy), the mHag peptide-specific CTLs will eliminate the mHag-positive patient's leukemic cells and, if of the patient's origin, also the patient's hematopoietic cells but will spare the patient's non-hematopoietic cells. If necessary, subsequent mHag-negative donor BMT will restore the patient's hematopoietic system. A universal approach is to generate "prefab" mHag peptide-specific CTLs by using mHag-negative healthy blood donors with frequent HLA-homozygous haplotypes. Patients who are mHag-positive (and their BM donors mHag-negative) and who match the HLA typing of the CTL donor can be treated with these "ready to be used" allo-peptide specific CTLS. Transduction of these CTLs with a suicide gene allows elimination of the CTLs in case adverse effects occur. For the sake of illustration a number of methods and applications is also given below in the experimental part.

EXPERIMENTAL PART

Graft-versus-Host Disease (GvHD) is a frequent and life-threatening complication after allogeneic HLA-identical bone marrow transplantation (BMT). Recipients of HLA-identical bone marrow develop acute or chronic Graft-versus-Host-Disease in respectively 36% and 49% [1,2]. Disparities in genes other than the MHC, referred to as minor histocompatibility (mH) antigens, are clearly involved in the development of GvHD after HLA-identical BMT. A recent retrospective analysis revealed the significant association between mismatching for the mH antigen HA-1 and the induction of GvHD after HLA-identical BMT [3]. Minor histocompatibility antigens are recognized by MHC restricted T cells and were shown to be peptides derived from intracellular proteins presented by MHC molecules [4,6]. Here we report the first identification of a polymorphic gene encoding an human mH antigen. The GvHD associated mH antigen HA-1 is a nonapeptide derived from the di-allelic KIAA0223 gene. The HA-1 allelic counterpart encoded by the KIAA0223 gene differs only at one amino acid from the mH antigen HA-1. Family studies demonstrated an exact correlation between the-KIAA0223 gene polymorphism and the HA-1 phenotype as was previously determined by recognition by the HA-1 specific CTL clones. The elucidation of the HA-1 encoding gene enables prospective HA-1 DNA typing of BMT donors and recipients to improve donor selection and prevention of GvHD.

Cytotoxic T cell clones specific for the mH antigen HA-1 have been isolated from three different patients with severe GvHD [7]. The mH antigen HA-1 is presented in the context of HLA-A2.1 and present in 69% of the HLA-A2.1 positive population [7]. HA-1 expression was demonstrated to be tissue specific and limited to cells of haematopoietic origin, including dendritic cells, Langerhans cells and leukemic cells [8-10]. Family analysis indicated a Mendelian mode of inheritance for HA-1 and segregation independent from the MHC complex [11]. Comparison of the T cell receptor (TCR) sequences of different HA-1 specific T cell clones derived from different individuals revealed conserved usage of the TCR Vb6.9 and conserved amino acids in the CDR3 region [12]. In a retrospective study, mismatching for a number of mH antigens was evaluated with regard to the association with GvHD after HLA-identical BMT. A single HA-1 mismatch between donor and recipient was significantly correlated with the induction of GvHD after HLA-identical BMT [3].

To identify the mH antigen HA-1, HLA-A2.1, molecules were purified from two HA-1 expressing EBV-transformed B lymnphoblastoid cell lines (EBV-BLCL) Rp and Blk. The HLA-A2.1 bound peptides were isolated by acid treatment and fractionation of the peptides was performed by multiple rounds of reverse phase HPLC. The fractions were analyzed for their capacity of inducing HA-1 specific lysis using T2 cells as target cells and an HA-1 specific CTL clone as effector cells in a $^{51}$Cr-release assay (FIG. 1-a). Fraction 24 contained HA-1 activity and was two times further fractionated with reverse phase HPLC using a different organic modifier (FIGS. 1b. and c.). Fraction 33 and 34 of the third HPLC fractionation showed HA-1 activity $^{51}$Cr-release assay and were analyzed by tandem mass spectrometry. Because over 100 different peptides were present in these fractions, around 40% of fractions 33 and 34 was chromatographed with an on-line microcapillary column effluent splitter. The fractions were simultaneously analyzed by tandem mass spectrometry and $^{51}$Cr-release assay (FIG. 1d.). Five peptide species (at m/z 550, 520, 513, 585 and 502) were specifically present in active fractions and absent in fractions without activity in the CML assay. Collision activated dissociation analysis of peptide candidate m/z 550 revealed the sequence YXTDRVMTV. (SEQ. I.D. NO. 3). X stands for Isoleucine or Leucine that cannot be discriminated with this type of mass spectrometer. However, a synthetic peptide with this sequence was not able to reconstitute the HA-1 epitope (results not shown). To determine which of the four remaining candidates was the HA-1 peptide, the second HA-1 purification of the EBV-BLCL Blk was evaluated HA-1 positive peptide fraction 33 of the second reverse phase HPLC fractionation was further chromatographed by microcapillary HPLC with a third organic modifier. A single peak of reconstituting activity was observed in a $^{51}$Cr-release assay (results not shown). Mass spectral analysis of these fractions revealed that only peptide candidate m/z 513 was present. This peptide was analyzed with collision activated dissociation analysis and sequenced as VXHDDXXEA (SEQ. I.D. NO. 4) (FIG. 2a). Isoleucine and Leucine variants of the peptide were synthesized and run on the microcapillary HPLC column. Only peptide VLHDDLLEA (SEQ. I.D. NO. 2) coeluted with the naturally processed peptide 513 (results not shown). Next, synthetic VLHDDLLEA (SEQ. I.D. NO. 2) added in different concentration to a CML assay with 3 different HA-1 specific CTL clones revealed recognition by all three clones of the peptide with a half maximal activity at 150–200 pM for all three clones (FIG. 2b). This demonstrated that the mH antigen HA-1 is represented by the nonapeptide VLHDDLLEA (SEQ. I.D. NO. 2).

Database searches performed to identify the gene encoding HA-1, revealed that the HA-1 peptide VLHDLLEA (SEQ. I.D. NO. 2) was identical for 8 out of 9 amino acids with the peptide VLRDDLLEA (SEQ. I.D. NO. 5) from the KIAA0223 partial complementary DNA (cDNA) sequence, derived from the acute myelogenous leukemia KG-1 cell line. Because HA-1 has a population frequency of 69%, we reasoned that the VLRDDLLEA (SEQ. I.D. NO. 5) peptide sequence might represent the HA-1 allelic counterpart present in the remaining 31% of the population. To elaborate on this assumption, we performed cDNA sequence analysis of the putative HA-1 encoding region of KIAA0223 in EBV-BLCL derived from a presumed HA-1 homozygous positive (vR), from a presumed HA-1 negative individual (DH) and from the KG-1 cell line (Table 1.). The HA-1 encoding region of KIAA0223 of the HA-1+/+ individual (vR) displayed two nucleotides differences from the KIAA0223 sequence in the databank, leading to the amino acid sequence VLHDDLLEA (SEQ. I.D. NO. 2) (designated HA-1$^H$). The HA-1 encoding region of KIAA0223 of the HA-1-/- individual (DH) showed 100% homology with the reported KIAA0223 sequence (designated HA-1$^R$). The KG-1 cell line expressed both KIAA0223 alleles. Because KG-1 does not express the restriction molecule HLA-A2.1 necessary for T cell recognition, we transfected KG-1 with HLA-A2.1 and used these cells as target cells in a $^{51}$Cr-release assay with the HA-1 specific T cell clone as effector cells. According to the cDNA sequence analysis results, the KG-1 cells were recognized by the HA-1 specific T cell clone (data not shown). This result suggested that the KIAA0223 gene forms a di-allelic system of which the HA-1$^H$ allele leads to recognition by the mH antigen HA-1 specific T cell clones. Two families, who were previously typed for HA-1 with HA-1 specific CTL, were studied on the cDNA level for their KIAA0223 polymorphism. The family members of family were screened for their KIAA0223 sequence polymorphism by sequencing the HA-1encoding sequence region. All HA-1 negative members displayed the HA-1$^R$ sequence, whereas all HA-1 positive members turned out to be heterozygous, thus carrying both HA-1 alleles (FIG. 3a). We subsequently designed HA-1 allele specific PCR primers to screen another family previously cellularly typed for HA-1. Both parents and one child were determined as heterozygous for HA-1, two HA-1 negative children homozygous for the HA-1$^R$ allele and one child homozygous for the HA-1$^H$ allele (FIG. 3b). The screening of both families showed an exact correlation of the HA-1 phenotype as determined by recognition by the HA-1 specific T cell clones and the KIAA0223 gene polymorphism.

To definitely prove that the KIAA0223 gene encodes the mH antigen HA-1, the HA-1 encoding sequence region of KIAA0223 of both the HA-1$^H$ and the HA-1$^R$ alleles were cloned in a eukaryotic expression vector and transiently transfected in HA-1 negative Hela cells in combination with HLA-A2.1. HA-1 specific T cell recognition of these transfected Hela cells was assayed using a TNF-α release assay. The Hela cells transfected with the HA-1$^H$ sequence containing vector were recognized by two HA-1 specific T cell clones (FIG. 3c). In contrast transfection of the HA-1$^R$ sequence containing vector did not lead to recognition. In conclusion, our results clearly demonstrate that the mH antigen HA-1 is encoded by the HA-1$^H$ allele of the KIAA023 gene.

Reconstitution and HLA-A2.1 binding assays were performed to determine the capacity of HA-1$^R$ peptide VLRDDLLEA (SEQ. I.D. NO. 5) to bind to HLA-A2.1 and to be recognized by the HA-1 specific T cell clones. The concentration of the HA-1$^R$ peptide that inhibited the binding of a fluorescent standard peptide to HLA-A2.1 by 50% (IC50) was 365 nM, falling in the intermediate binders, whereas the IC50 of the HA-1$^H$ peptide was 30 nM, which is in the range of high affinity binders (FIG. 4a) [13,14]. Different concentrations of VLRDDLLEA (SEQ. I.D. NO. 5) were tested in a $^{51}$Cr-release assay with three HA-1 specific T cell clones. One out of three clones (3HA15) tested showed recognition of the HA-1$^R$ peptide, but only at 1000 times higher peptide concentration than that necessary for the recognition of the HA-1$^H$ peptide (FIG. 4b). As the binding affinity of the two peptides to HLA-A2.1 differs only 10-fold, it can be concluded that all the T cell clones specifically recognize the HA-1$^H$ peptide.

The 3HA15 T cell clone, recognizing the HA-1$^R$ peptide at high concentrations, does not recognize HA-1$^R$ homozygous individuals. This suggests that the VLRDDLLEA (SEQ. I.D. NO. 5) peptide is not presented by HLA-A2.1 or presented below the detection limit of the T cell. To determine whether the HA-1$^R$ peptide VLRDDLLEA (SEQ. I.D. NO. 5) was presented by HLA-A2.1, HLA-A2.1 bound peptides were eluted from a HA-1$^R$ homozygous EBV-BLCL and fractionated with reverse phase HPLC. The synthetic HA-1-peptide VLRDDLLEA (SEQ. I.D. NO. 5) was run on reverse HPLC to determine at which fraction this peptide eluted. The corresponding HPLC fractions derived from the HA-1$^R$ expressing EBV-BLCL were analyzed using mass spectrometry. Presence of peptide VLRDDLLEA (SEQ. I.D. NO. 5) could not be detected (results not shown), indicating that this peptide is not present or presented by HLA-A2.1 in very low amounts on the cell surface. This is most likely due to the 10-fold lower binding affinity of the peptide for HLA-A2. 1. The supposed absence of the HA-1$^R$ peptide in HLA-A2.1 indicates that this allele must be considered as a null allele with regard to T cell reactivity. This implicates that only BMT from an HA-1$^{R/R}$ (HA-1-) donor to HA-1$^{H/H}$ or HA-1$^{R/H}$ (HA-1+) recipient direction and not the reverse would be significantly associated with GvHD. This is indeed observed in a retrospective study in which HLA-2.1 positive BMT pairs were typed for HA-1 [3]. However, HA-1$^R$ derived peptides may bind to other HLA alleles and possibly be recognized by T cells. If the latter peptides are not generated and presented by the HA-1$^H$ allele, then T cell reactivity towards the HA-1$^R$ allele may be envisaged and GvHD in that direction may occur.

Only a few murine and human mH antigens have been identified so far on the peptide and gene level. Two murine mH antigens are encoded by mitochondral proteins, leading to respectively four and two alleles [15-17]. In addition, two murine H-Y mH antigens were shown to be peptides encoded by Y-chromosome located genes [18-21]. The human SMCY gene, located on the Y chromosome, encodes the HLA-B7 and the HLA-A2.1 restricted H-Y mH antigens [5,6]. Of the human non-sex linked mH antigens, only the mH antigen HA-2 has been sequenced on the peptide level, but the HA-2 encoding gene remained unknown [4]. The identification of the gene encoding the mH antigen HA-1 is the first demonstration that human mH antigens are derived from polymorphic genes. The HA-1 encoding KIAA0223 gene has two alleles differing in two nucleotides leading to one single amino acid difference. However, because the KIAA0223 gene has not been fully sequenced yet, it remains to be established whether additional amino acid polymorphisms between the two alleles of this gene are present. Because the HA-1 mH antigen is the only known human mH antigen that is correlated with the development of GvHD after BMT the results of our study are of significant clinical relevance [3]. Although the numbers of different human mH antigens is probably high, it is envisaged that only few immunodominant mH antigens can account for the risk for GvHD [22]. Identification of those human immunodominant mH antigens and screening for those antigens may result in a significant decrease in GvHD after BMT. Here we describe the first elucidation of a polymorphic gene encoding the immunodominant mH antigen HA-1. This enabled us to design HA-1 allele specific PCR primers for pre-transplant donor and recipient typing to improve donor selection and thereby prevention of HA-1 induced GvHD development.

It also enabled us to start targeting leukemic cells carrying minor antigens present on hematopoietic cells. One way of arriving at agents targeting leukemic cells, is the ex vivo preparation of CTL's. This is explained herein. Allogeneic bone marrow transplantation (BMT) is a common treatment of hematological malignancies [29]. Recurrence of the underlying malignancy is a major cause of treatment failure [30,31]. Relapsed CML patients can be successfully treated by donor lymphocyte infusions (DLI) [32,33], but the treatment is less effective for relapsed AML and ALL [32,33], and is frequently complicated with Graft versus Host Disease (GvHD) [32-34]. Donor derived CTLs specific for patients' minor histocompatibility antigens (mHags) play an important role in both GvHD and GvL reactivities [10, 35-38]. mHags HA-1 and HA-2 induce HLA-A2 restricted CTLs in vivo. mHags HA-1 and HA-2 are exclusively expressed on hematopoietic cells including leukemic cells [10,36] and leukemic precursors [37,38], but not on cells of the GvHD target organs such as skin fibroblasts, keratinocytes or liver cells [8]. Recently the chemical nature of the mHags HA-1 and HA-2 was unraveled [4,39]. Here we report on the feasibility of ex vivo generation of mHag HA-1 and HA-2 specific CTLs from unprimed mHag HA-1 and/or HA-2 negative healthy blood donors with the purpose of adoptive immunotherapy of relapsed leukemia with a low risk of GvHD. To define the optimal antigen presenting cell (APC) for ex vivo generation of HA-1 and HA-2 specific CTLs, we prepared peripheral blood mononuclear cells (PBMC), monocytes, peripheral blood circulating dendritic cells (PBDC) or dendritic cells derived from bone marrow CD34+ progenitor cells (BMDC) from fifteen HLA-A2 positive, HA-1 or HA-2 negative healthy blood donors. These APCs were pulsed with HA-1 and/or HA-2 synthetic peptides and used to stimulate autologous unprimed CD8+ T cells. The attempts to induce HA-1 or HA-2 specific CTLs using monocytes or PBMC were not very successful. PBMC induced in only one out of three attempts HA-2 specific CTLs. Using monocytes, we generated two HA-1 peptide specific CTLs, but these CTLs did not lyse HA-1 positive target cells in our experiments (data not shown). It is possible that these "peptide specific" CTLs have a lower affinity for the naturally expressed HA-1 antigen, but this does not mean that these cells cannot be used for generating CTL's against minor antigens.

PBDC were enriched from nine individuals to induce HA-1 or HA-2 specific CTLs. In the four cases where the preparations had a purity of less than 30% the CTLs lysed peptide loaded target cells but not mHag positive target cells (data not shown). In contrast, in all cases (n=5) where PBDC purity was 30% or more, the CTLs not only recognized mHag negative, peptide pulsed target cells, but also mHag positive EBV-LCL, demonstrating the recognition of the naturally expressed ligand (FIG. 1). These results underscore the superior capacity of DC to induce T cell responses from naive precursors and confirm the current opinion [40]. Similarly, two BMDC induced CTLs that recognized both peptide pulsed target cells and HA-1 positive target cells (FIG. 5). No cytotoxic activity was observed against autologous PHA stimulated T cell blasts (PHA blasts) or against mHag negative ERV-LCL. Thus, autoreactivity nor "third-party" alloantigen reactivity was observed. Several HA-1 or HA-2 specific CTL clones isolated from these CTLs did not react against autologous cells either. These results show that HA-1 and HA-2 specific CTLs can be safely transferred to patients after BMT.

The ex vivo induced HA-1 and HA-2 specific CTLs were tested for their hematopoietic cell restricted reactivity and compared with the in vivo induced HA-1 and HA-2 specific CTLs (FIG. 6). PHA blasts, but not fibroblasts (neither after IFN-γ/TNF-α stimulation) were recognized by both ex vivo and in vivo induced HA-1 and HA-2 specific CTLs. Fibroblasts, were only lysed after pulsing with the mHag peptides, demonstrating their susceptibility to CTL mediated lysis. These data not only confirm that the HA-1 and HA-2 antigens are functionally expressed solely on hematopoietic cells [8], but also show that adoptive transfer of HA-1 or HA-2 specific CTLs to HA-1 or HA-2 positive patients will spare the patient's non-hematopoietic tissues and cells. Thus, upon adoptive transfer of HA-1 and HA-2 specific CTLs, a low risk of GvHD is to be expected. Some precaution may be necessary since we have previously demonstrated that HA-1 disparity between patient and donor is associated with the development of GvHD in adults[3]. Therefore, we do not transfer the CTLs before 50–60 days post BMT. It is assumed that most recipient hematopoietic cells are then replaced by donor cells. Alternatively, one may transduce the HA-1 and HA-2 specific CTLs with a suicide gene which will make the in vivo elimination of cells possible if adverse effects occur [41]. The ex vivo induced HA-1 and HA-2 specific CTLs were subsequently analyzed for cytolytic activity against, for this study most relevant target cells, leukemic cells. In vivo induced HA-1 and HA-2 specific CTLs and an HLA-A2 specific alloreactive CTL were used as control effector cells. As shown in FIG. 7. AML and ALL cells were lysed by HLA-A2 specific alloreactive CTL, and by in vivo induced HA-1 and HA-2 specific CTLs, indicating that the leukemic cells were positive for HLA-A2 and expressed HA-1 or HA-2 antigens. As expected the ex vivo induced CTLs lysed the leukemic cells comparable to the control effector cells. These results show that HA-1 and HA-2 specific CTLs can also be used as therapy for relapsed AML or ALL, which are resistant to DLI treatment. The level of cytotoxicity could be significantly enhanced following IFN-γ and TNF-α treatment of the leukemic cells indicating that cytokines upregulated HLA class I expression on the leukemic cells. HA-1 and HA-2 specific CTL clones produce IFN-γ and TNF-α ex vivo. It is possible that cytokine production by HA-1 and HA-2 specific CTLs occurs in vivo as well. Alternatively the efficacy of adoptive immunotherapy with HA-1 and HA-2 specific CTLs may be enhanced by co-administration of IFN-α in resistant cases. The feasibility of adoptive immunotherapy with ex vivo generated CTLs depends also on their expandability to sufficient numbers. We therefore scored the expansion rates of HA-1 and HA-2 specific CTLs generated by DC. The results indicate that sufficient numbers of CTLs for adoptive immunotherapy can be obtained if T cell cultures will be started with $5 \times 10^7$ responder cells. For instance, two HA-2 specific CTLs induced by PBDC showed expansion rates of above 9, 25 and 8 fold at the second, third, and fourth week, respectively. These expansion rates translate into an estimated total yield of $3 \times 10^9$–$10^{10}$ CTLs at the end of the fourth week. The expansion kinetics of the HA-1 specific CTLs were slower, but the cells expanded consistently with doubling times of 2–3 days during each restimulation. It is estimated that $10^9$ HA-1 specific CTLs can be obtained after five weeks of culture.

In conclusion, our results show for the first time that mHag HA-1 and HA-2 specific CTLs can reproducibly be generated ex vivo from HLA-A2 positive, mHag HA-1 and/or HA-2 negative healthy blood donors using dendritic cells pulsed with synthetic peptides. After the successful application of EBV-specific CTLs as specific adoptive immunotherapy of EBV-related malignancies [42], our results now provide a new possibility for the treatment of relapsed, HA-1 and/or HA-2 positive leukemia patients with HA-1 or HA-2 specific CTLs induced ex vivo from their HLA identical, mHag negative bone marrow donors.

METHODS

Cell culture. The CD8+ HLA-A2.1 restricted HA-1 specific cytotoxic T cell clones 3HA15, clone 15 and 5W38 were derived from PBMC of two patients who had undergone HLA identical bone marrow transplantation [7,23]. The clones were cultured by weekly stimulation with irradiated allogeneic PBMC and BLCL in RPMI-1640 medium containing 15% human serum, 3 mM 1-glutamin, 1% Leucoagglutinin-A and 20 U/ml rII-2. The HLA-A2.1 positive HA-1 expressing EBV transformed B cell lines (BLCL) Rp and Blk were maintained in IMDM containing 5% FCS. The KG-1 and T2 cell lines were cultured in 1640 medium containing 3 mM 1-glutamin and 10% FCS.

$^{51}$Cr-release assay. HPLC fractions and synthetic peptides were tested in a $^{51}$Cr-release assay as described [24]. 2500 $^{51}$Cr labeled T2 cells in 25 ml were incubated with 25 ml peptide dissolved in Hanks 50 mM Hepes for 30 minutes at 37° C. Cytotoxic T cells were added in an end volume of 150 ml. When HPLC peptide fractions were tested, T2 was incubated with 2 mg/ml MA2.1 during the $^{51}$Cr labelling. After 4 hours at 37° C. the supernatants were harvested.

Peptide purification. Peptides were eluted out of purified HLA-A2.1 molecules as earlier described [24]. Briefly, HLA-A2.1 molecules were purified two times from 90.10$^9$ HLA-A2.1 positive EBV-BLCL by affinity chromatography with BB7.2 coupled CNBR-activated sepharose 4B beads (Pharmacia LKB) and extensively washed. Peptides were eluted from the HLA-A2.1 with treatment with 10% acetic acid, further acidified by 1% TFA and separated from the HLA-A2.1 heavy chain and B2-microglobulin by filtration over a OkD Centricon (Amicon) filter. Peptides were fractionated using reverse phase micro HPLC (Smart System, Pharmacia). For the first purification, three rounds of HPLC fractionation were used to purify the HLA-A2.1 restricted HA-1 active peptide fractions from 90.10$^9$ Rp cells. The first fractionation consisted of buffer A: 0.1% HFBA in H20, buffer B: 0.1% HFBA in acetonitrile. The gradient was 100% buffer A (0 to 20 min), 0 to 15% buffer B (20 to 25 min) and 15 to 70% buffer B (25 to 80 min) at a flow rate of 100 ml/min. Fractions of 100 ml were collected. Fraction 24 of the first gradient was further fractionated. The second fractionation consisted of buffer A: 0.1% TFA in H2O, buffer B: 0.1% TFA in acetonitrile. The gradient was 100% buffer A (0 to 20 min), 0 to 12% buffer B (20 to 25 min), and 12 to 50% buffer B (25 to 80 min) at a flow rate of 100 ml/min. Fractions of 100 ml were collected. A shallower third gradient was used to further purify fraction 27 that contained HA-1 activity. The gradient was 100% buffer A (0 to 29 min), 0 to 18% buffer B (29 to 34 min), 18% buffer B (34 to 39 min), 18 to 23.9% buffer B (39 to 98 min) at a flowrate of 100 ml/min. 1/180 to 1/45 of the starting material was used to test for positive fractions in the $^{51}$Cr-release assay. Comparable HPLC fractionations were used for the second purification of HLA-A2.1 restricted HA-1 active peptide fractions from 90.10$^9$ Blk 40% of the HA-1 containing fraction 33 of the second HA-1 purification was used for an additional reverse phase microcapillary HPLC fractionation. Buffer A was 0.1% triethyl amine (TEA) in water buffered to pH 6.0 with acetic acid and buffer B was 0.085% TEA in 60% acetonitrile buffered to pH 6.0 with acetic acid. The gradient was 100% buffer A (0 to 5 min), 0 to 100% B (5 to 45 min) at a flow rate of 0.5 ml/min. Fractions were collected in 50 ml of 0.1% acetic acid every minute for 5 to 15 minutes, every 30 seconds from 15 to 20 minutes, every 20 seconds from 20 to 40 minutes, and every 30 seconds from 40 to 45 minutes. For each fraction collected, 20% was used to test for HA-1 activity and 80% was used to obtain mass spectral data.

Mass spectrometry. Fractions from third dimension HPLC separation of the Rp purification that contained the HA-1 activity were analyzed by mnicrocapillary HPLC-electrospray ionization mass spectrometry [25]. Peptides were loaded onto a C18 microcapillary column (75 mm i.d.×10 cm) and eluted with a 34 minute gradient of 0 to 60% B, where solvent A was 0.1M acetic acid in water and solvent B was acetonitrile at a flow-rate of 0.5 ml/min. One-fifth of the effluent was deposited into the wells of a 96-well plate containing 100 ml of culture media in each well (10 seconds fractions), while the remaining four-fifths was directed into the electrospray source of the TSQ-70U. Mass spectra and CAD mass spectra were recorded on a Finnigan-MAT TSQ-7000 (San Jose, Calif.) triple quadruple mass spectrometer equipped with an electrospray ion source.

HLA-A2.1 peptide binding assay. A quantitative assay for HLA-A2.1 binding peptides based on the inhibition of binding of the fluorescent labeled standard peptide Hbc 18–27 F to C6 (FLPSDCFPSV) (SEO. I.D. NO. 17) to recombinant HLA-A2.1 protein and B2-microglobulin was used [26,27]. In short, HLA-A2.1 concentrations yielding approximately 40–60% bound fluorescent standard peptide were used with 15 pmol/well (150 nM) B2-microglobulin (Sigma). Various doses of the test peptides were coincubated with 100 fmol/well (1 nM) fluorescent standard peptide, HLA-A2.1 and B2-microglobulin for 1 day at room temperature in the dark in a volume of 100 ml in assay buffer. The percent of MHC-bound fluorescence was determined by gel filtration and the 50% inhibitory dose was deduced for each peptide using one-site competition non-linear regression analysis with the prismgraph software. Synthetic peptides were manufactured on a Abimed 422 multiple peptide synthesizer (Abimed, Langenfeld, Germany) and were more than 90% pure as checked by reverse phase HPLC.

RT-PCR Amplification and Sequencing of KIAA0223 Region Coding for HA-1

Total or mRNA was prepared from BLCL using the RNAzol method (Cinaa/Biotecx Laboratories, Houston, Tex.) or according to manufacturer's instructions (QuickPrep mRNA purification Kit, Pharmacia Biotech). CDNA was synthesized with 1 mg RNA as template and with KIAA0223 based reverse primer 5'-GCTCCTGCATGACGCTCTGTCTGCA-3' (SEQ. I.D. NO.6). To amplify the HA-1 region of KIAA0223 the following primers were used: Forward primer 5'-GACGTCGTCGAGGACATCTCCCAT-3' (SEQ. I.D. NO.7) and reverse primer 5'-GAAGGCCACAGCAATCGTCTCCAGG-3' (SEQ. I.D. NO. 8). Cycle parameters used were denaturation 95° C., 1 min, annealing 58° C., 1 min and extension 72° C., 1 min (25 cycles). The PCR-products were purified using the Magic PCR-Preps DNA purification System (Promega) and direct cloned using the pMosBlue T-vector kit (Amersham LIFE SCIENCE). Six independent colonies from each individual were sequenced using the T7-sequencing kit (Pharmacia Biotech).

HA-1 Allele Specific PCR Amplification

In the case of HA-1 allele specific PCR amplification, cDNA was synthesized as described above. A PCR amplification was performed with allele specific forward primers: for the HA-1$^H$ allele primer H1: 5'-CCT-TGA-GAA-ACT-TAA-GGA-GTG-TGT-GCT-GCA-3' (SEQ. I.D. NO. 9), for the HA-1$^R$ allele primer R1: 5'-CCT-TGA-GAA-ACT-TAA-GGA-GTG-TGT-GTT-GCG-3' (SEQ I.D. NO. 10) 0 and for both reaction the reverse primer as described above was used. Cycle parameters used were denaturation 95° C., 1 min, annealing 67° C., 1 min and extension 72° C., 1 min (25 cycles).

Cloning and Expression of HA-1$^H$ and HA-1$^R$ Allelic Region of KIAA0223

A forward KIAA00223 based PCR primer containing an ATG startcodon (5'-CCG-GCA-TGG-ACG-TCG-TCG-AGG-ACA-TCT-CCC-ATC-3') (SEQ. I.D. NO. 11) and a reverse KIAA0223 based PCR primer containing a translational stop signal (5'-CTA-CTT-CAG-GCC-ACA-GCA-ATC-GTC-TCC-AGG-3') (SEQ. I.D. NO. 12) were designed and used in a RT-PCR reaction with cDNA derived from an homozygous HA-1$^H$ and a homozygous HA-1$^R$ BLCL. Cycle parameters used were denaturation 95° C., 1 min, annealing 60° C., 1 min and extension 72° C., 1 min (25 cycles). The desired PCR-products were purified using the Magic PCR-Preps DNA purification System (Promega). The purified DNA was direct cloned using the pMosBlue T-vector kit (Amersham LIFE SCIENCE) and recloned in the eukaryotic pCDNA3.1(+) vector under the control of a CMV promotor. Transient cotransfections were performed with HLA-A2.1 in Hela cells using DEAE-Dextran coprecipitation. After 3 days of culture HA-1 specific T cells were added and after 24 hours the TNF-α release was measured in the supernatant using WEHI cells [28].

Peptides: HA-1 and HA-2 peptides were synthesized using a semi automatic multiple peptide synthesizer [4,39]. The purity of the peptides was checked by reversed phase high pressure liquid chromatography (HPLC).

Antigen Presenting Cells:

PBMC were isolated by ficoll-hypaque density gradient separation of blood collected with manual hemapheresis.

Monocytes were isolated by plastic adherence during PBDC enrichment.

PBDC were enriched from PBMC by depletion of T cells, monocytes, B and NK cells as described earlier. Briefly, T cells were depleted by sheep red blood erythrocyte rosetting. Non-T cells were cultured 36 h at 37° C. in RPMI+10% autologous plasma. After depleting monocytes non adherent cells were layered on 14.5% metrizamide gradients and centrifugated. The light density PBDC were recovered from the interphase. PBDC were identified by FACS being negative for CD3, CD14, CD16 and CD19 and positive for HLA-DR The preparations contained 2–6×10$^6$ cells with a DC content of 20–50%. In some cases the light density cells were further depleted from CD14 and CD19 cells using antibody coated magnetic beads.

BMDC were differentiated from bone marrow CD34+ cells (isolated using CD34+ isolation kit, MACS, Bergisch Gladbach, Germany) by culturing with 100 ng/ml FLT3-ligand (Genzyme, Leuven; Belgium), 30 ng/ml IL-3, 25 ng/ml SCF (Genzyme) 50 U/ml TNF-α (Genzyme), 250 U/ml GM-CSF (Genzyme) for 10 to 14 days. The cultures contained 20–60%/ DC as detected by high levels of DR and negative expression of CD3/CD14/CD16/CD19.

Ex vivo induction of HA-1 and HA-2 specific CTLs: APC were pulsed with HA-1 or HA-2 peptides (both 10 mg/ml) for 90 min. at 37° C. in serum free AIM-V medium. After washing, APC and 10–15×10$^6$ responder cells (CD4 depleted autologous PBMC) were cultured at different APC responder cell ratios depending on the type of APC (5:1, 1:3 and 1:10 for PBMC, Mo and DC, respectively) in 24 well culture plates. Culture medium was RPMI supplemented with 10% autologous plasma, 1 U/ml IL-2 (Cetus), 1 U/ml IL-12 (Genzyme). The cells were kept at 37° C. in a humidified, 5% $CO_2$-air mixture. At day 5, 10 U/ml of IL-2 was added. Starting from day seven, the T cell cultures were restimulated weekly with peptide pulsed autologous monocytes. 10 U/ml of IL-2 was added 24 h. after each restimulation. The T cell lines were expanded with 10–20 U/ml IL-2 containing culture medium.

Cytotoxicity ($^{51}$Cr release) assays: Standard 4 h $^{51}$Cr release assays using PHA-blasts, EBV-BLCL and fibroblasts and leukemic cells as target cells were performed as described before [8]. The percent specific lysis was calculated using the following formula: 100×(cpm experimental release-cpm spontaneous release)/(cpm maximal release-cpm spontaneous release).

Target cells: EBV-BLCL were generated as described before [8] and cultured in RPMI plus 10% FCS. PHA activated T cell blasts (PHA-blasts) were obtained by stimulation of PBMC with 0.1 mg/ml PHA (Wellcome) during 72 h. PHA-blasts were expanded with medium containing 20 U/ml IL-2. Skin fibroblasts of an HLA-A2+, HA-1+, HA-2+ healthy individual were isolated, cultured and tested as described before [8]. In short, fibroblasts were typsinized and cultured in the wells of 96 well flat bottomed microtiter culture plates at a concentration of 3×10$^3$ cells/well with or without addition of IFN-γ and TNF-α (both 300 U/ml) during 72 h. When indicated, target cells were pulsed with HA-1 or HA-2 peptides (both 10 mg/ml) during $^{51}$Cr labeling.

Leukemia patients' (AML or ALL) PBMC or BM containing>95% morphologically recognizable malignant cells were assigned as leukemic cells. Leukemic cells were thawed and cultured in RPMI plus 10% human serum for 72 h with or without addition of IFN-γ and TNF-α (both 300 u/ml) before using as target cells.

In vivo induced mHag specific T cell clones: In vivo induced, mHag HA-1 and HA-2 specific CD8+ CTL clones were isolated from post BMT leukemia patients, and were documented in detail [35].

BRIEF DESCRIPTION OF THE DRAWINGS

Table 1. KIAA0223 sequence polymorphism in mH HA-1 positive and HA-1 negative individuals.

Sequencing of HA-1 region in KIAA0223 gene in HA-1 +/+ and HA-1 −/− homozygous individuals and KG-1 revealed two alleles differing in two nucleotides resulting in a one amino acid difference (H to R) and designated HA-1$^H$ and HA-1$^R$. For DH and vR 6 independent PCR products were sequenced. For KG-1 8 PCR products were sequenced.

(FIG. 1a). Peptides were eluted from 90.10$^9$ HA-1 and HLA-A2.1 positive Rp cells and separated using reverse phase HPLC with HFBA as organic modifier. (FIG. 1b.) Fraction 24 of the first HPLC dimension that contained HA-1 activity was further fractionated by reverse phase HPLC with TFA as organic modifier. (FIG. 1c.) HA-1 containing fraction 27 of the second gradient was further chromatographed with a third shallower gradient consisting of 0.1% acetonitrile/min. Background lysis of T2 by the CTL in the absence of any peptides was in a 3%, in b and c 0%. Positive control lysis was in a 99%, in b 74% and in c 66%.

FIG. 2. Sequencing of mH HA-1 peptide by tandem mass spectrometry.

REFERENCES

Figure 1:
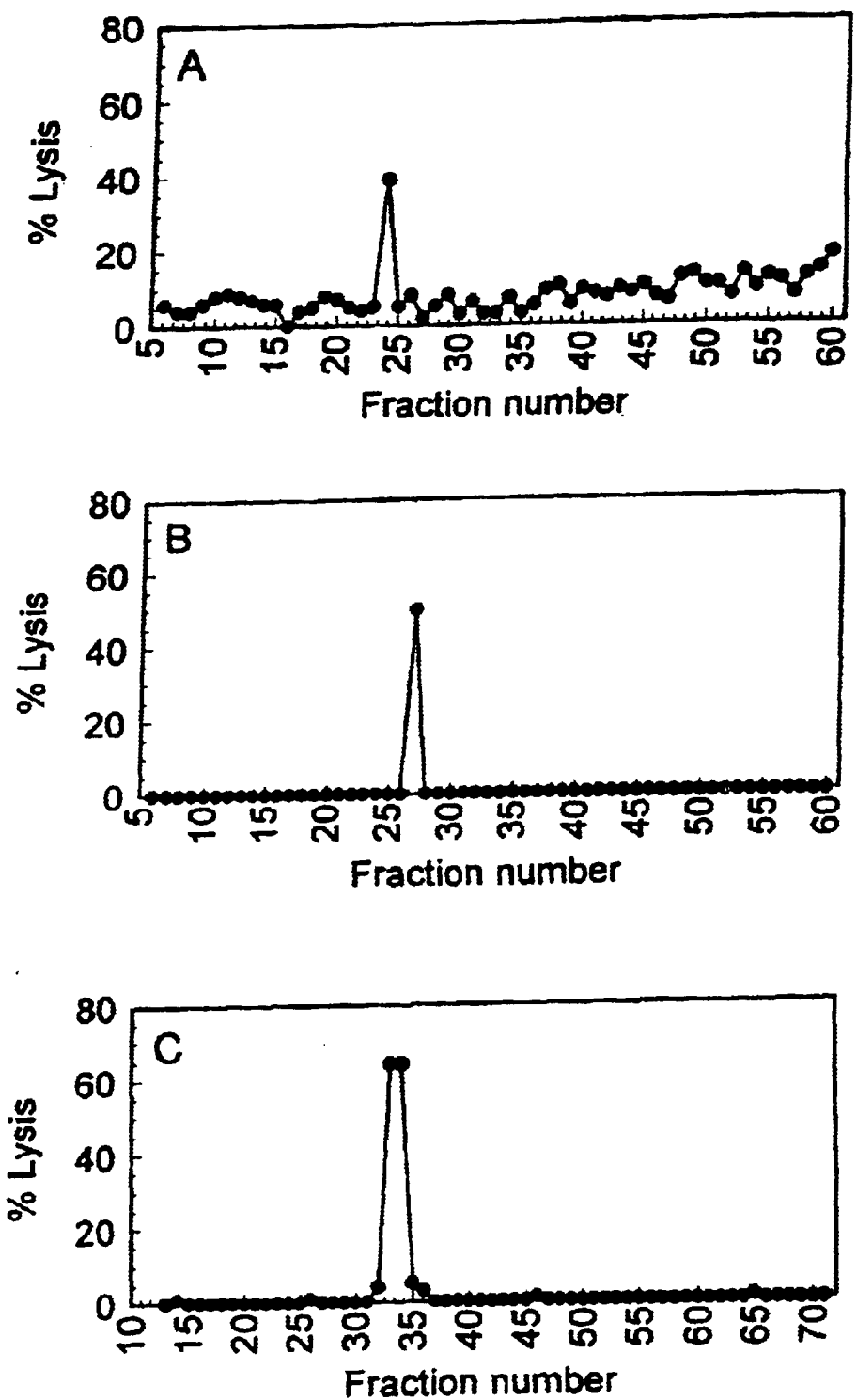
FIG. 1 Reconstitution of HA-1 with HPLC fractionated peptides eluted from HLA-A2.1 molecules in a $^{51}$Cr-release assay with mH HA-1 specific T cell clone 3HA15.
Figure 1D:
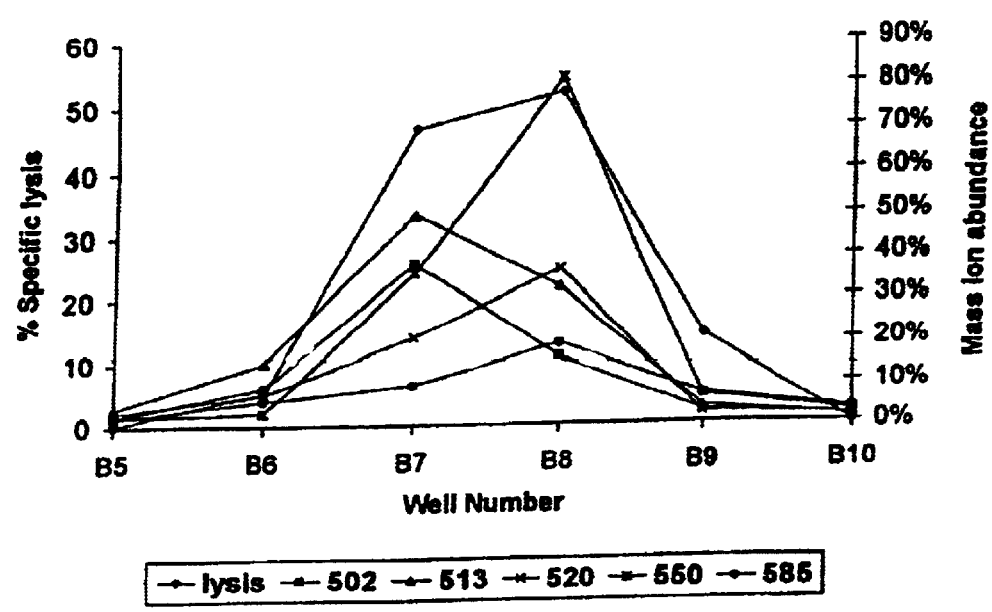
(FIG. 1d.) Determination of candidate HA-1 peptides. HPLC fraction 33 from the separation in FIG. 1c. was chromatographed with an on-line microcapillary column effluent splitter and analyzed by electrospray ionization mass spectrometry and a $^{51}$Cr-release assay. HA-1 reconstituting activity as percent specific release was compared with the abundance of peptide candidates measured as ion current.
Figure 2A:
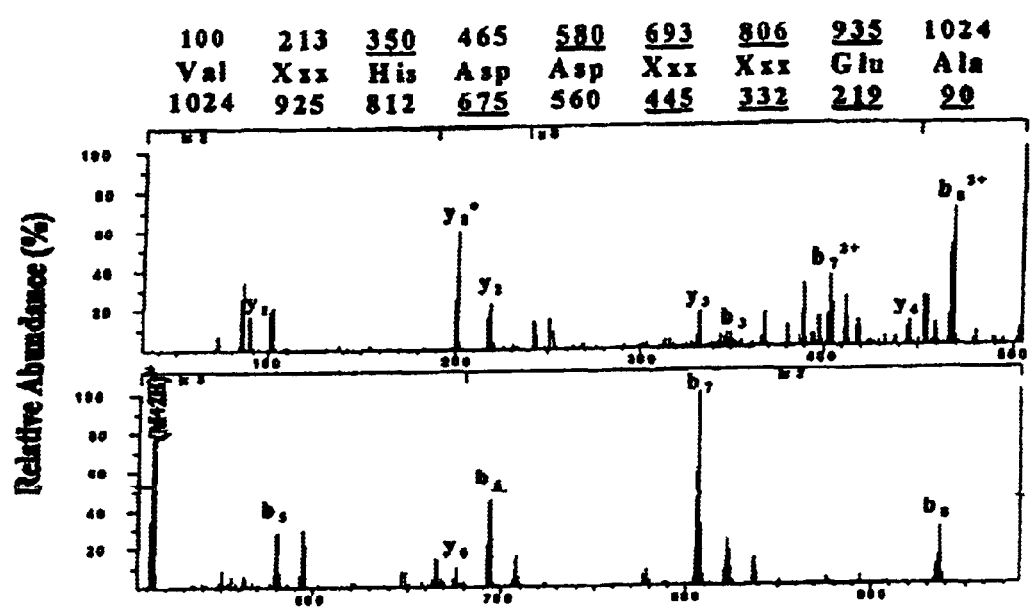
(FIG. 2a.) Collision activation dissociation mass spectrum of peptide candidate with m/z of 513.
Figure 2B:
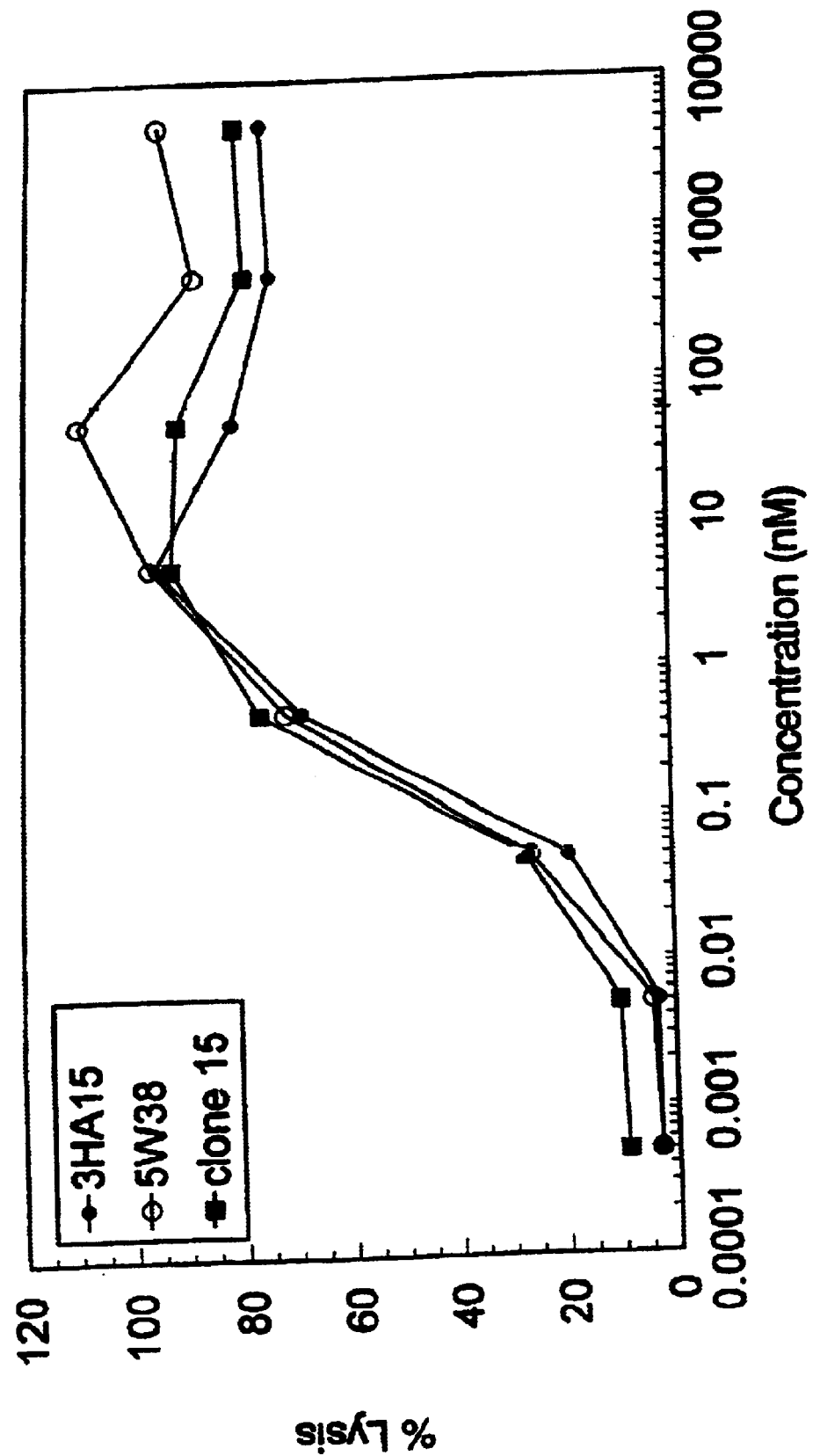
(FIG. 2b.) Reconstitution assay with different concentrations of synthetic mH HA-1 peptide with three HA-1 specific T cell clones, 3HA15, clone 15 and 5W38. Background lysis of T2 by the CTL in the absence of any peptide was for 3HA15 4%, for clone 15 10% and for 5W38 2%. Positive control lysis was for 3HA15 46%, for clone 15 47% and 5W38 48%.
Figure 3A:
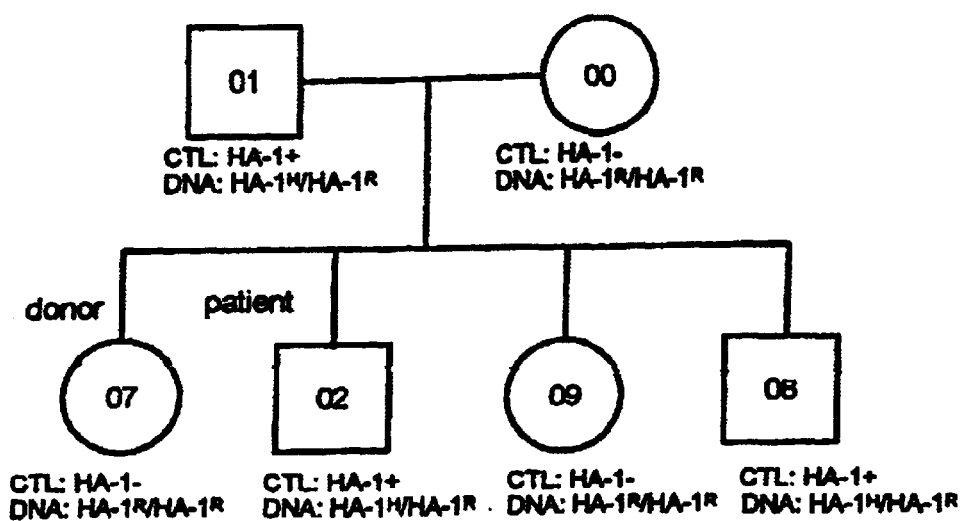
(FIG. 3a.) The HA-1 region of KIAA0223 was sequenced in a HA-1 mH antigen typed family. 6 PCR products of each family member were sequenced. Family members 00, 07 and 09 expressed the HA-1$^R$ in all 6 PCR products. Family member 01 expressed the HA-1$^H$ allele in 2 PCR products and the HA-1$^R$ allele in 4 PCR products. Family member 02 expressed the HA-1$^H$ allele in 3 PCR products and the HA1$^R$ allele in 3 PCR products. Family member 08 expressed the HA-1$^H$ allele in 4 PCR products and the HA-1$^R$ allele in 2 PCR products (FIG. 3b) HA-1 allele specific PCR reaction in a HA-1 mH antigen typed family correlated exactly with the HA-1 phenotype. The sizes of the resulting PCR products were consistent with the expected sizes deduced from the cDNA sequence.
Figure 3B:
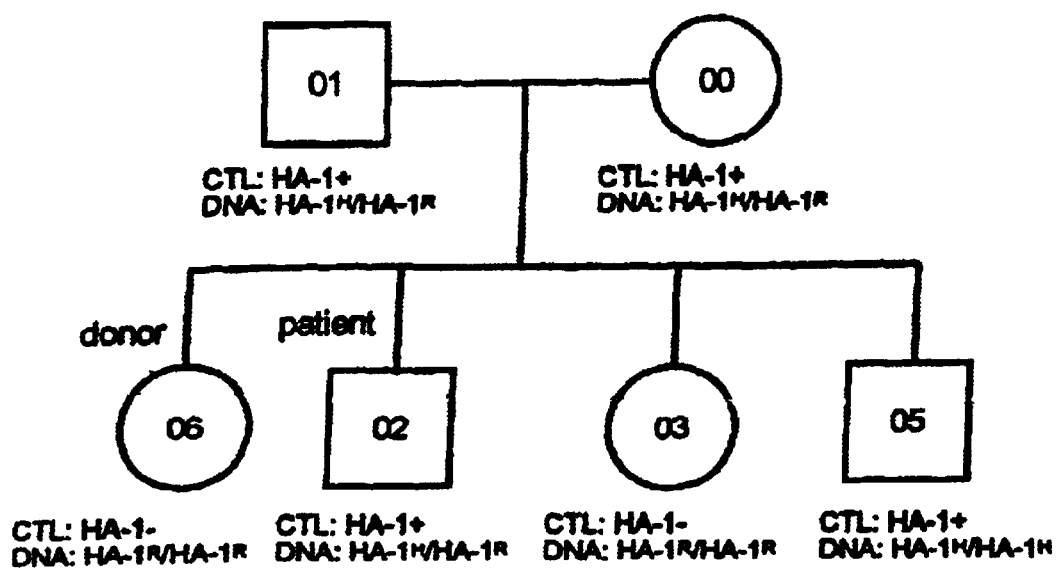
FIG. 3. KIAA0223 polymorphism exactly correlated with mH antigen HA-1 phenotype.
(FIG. 3c.) Transfection of the HA-1$^H$ allele of KIAA0223 leads to recognition by mH HA-1 specific T cells. The HA-1$^H$ and the HA-1$^R$ coding sequence of KIAA0223 were together with HLA-A2.1 transfected into Hela cells. After 3 days the HA-1 specific CTL clones 5W38 and 3HA15 were added and after the 24 hours TNF-α release was measured in the supernatant. The clone Q66.9 is specific for the influenza matrix peptide 58–66. No TNF-α production was observed after transfection of the pcDNA3.1 (+) vector alone (results not shown).
Figure 3B:
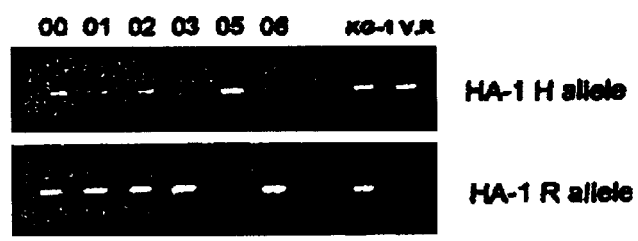
Figure 3C:
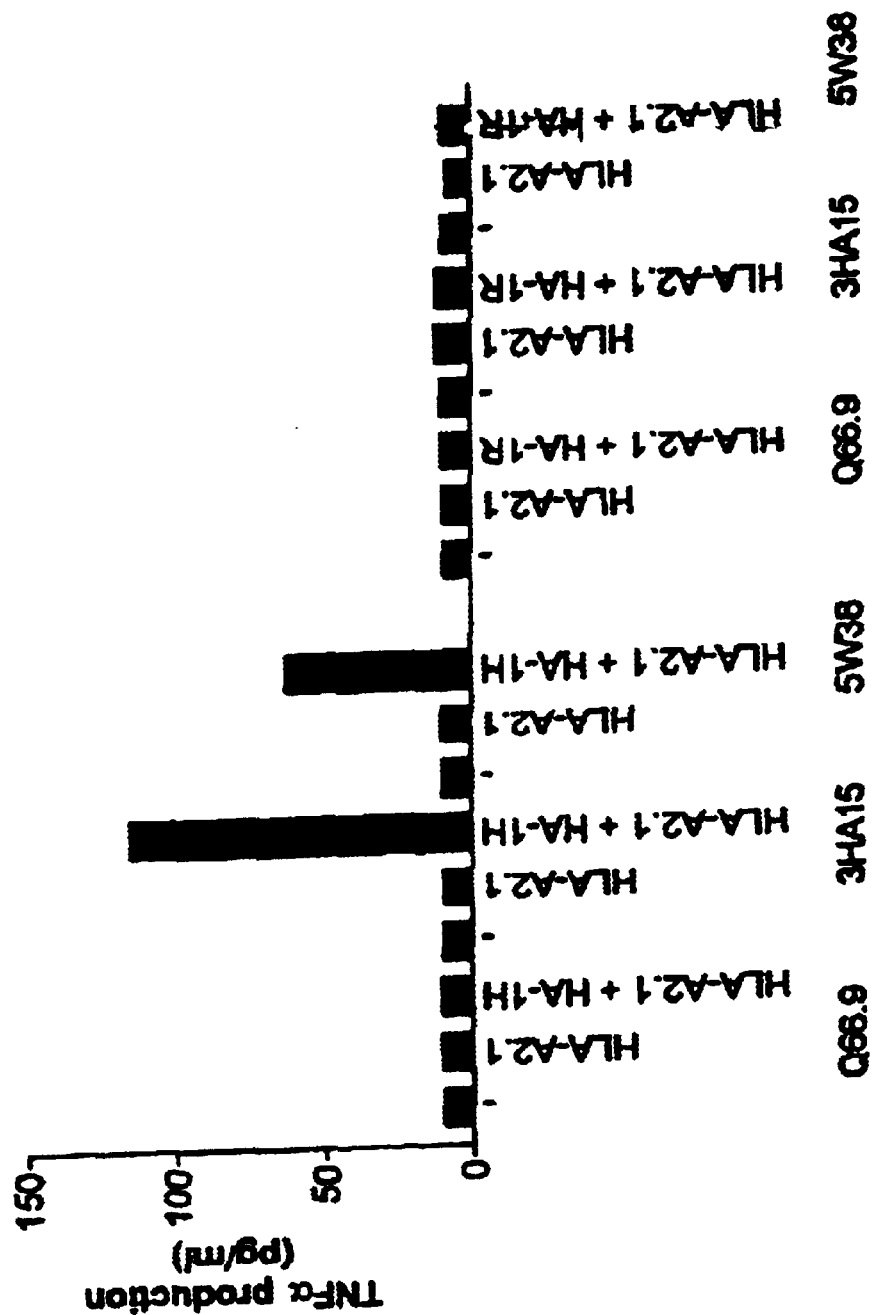
Figure 4A:
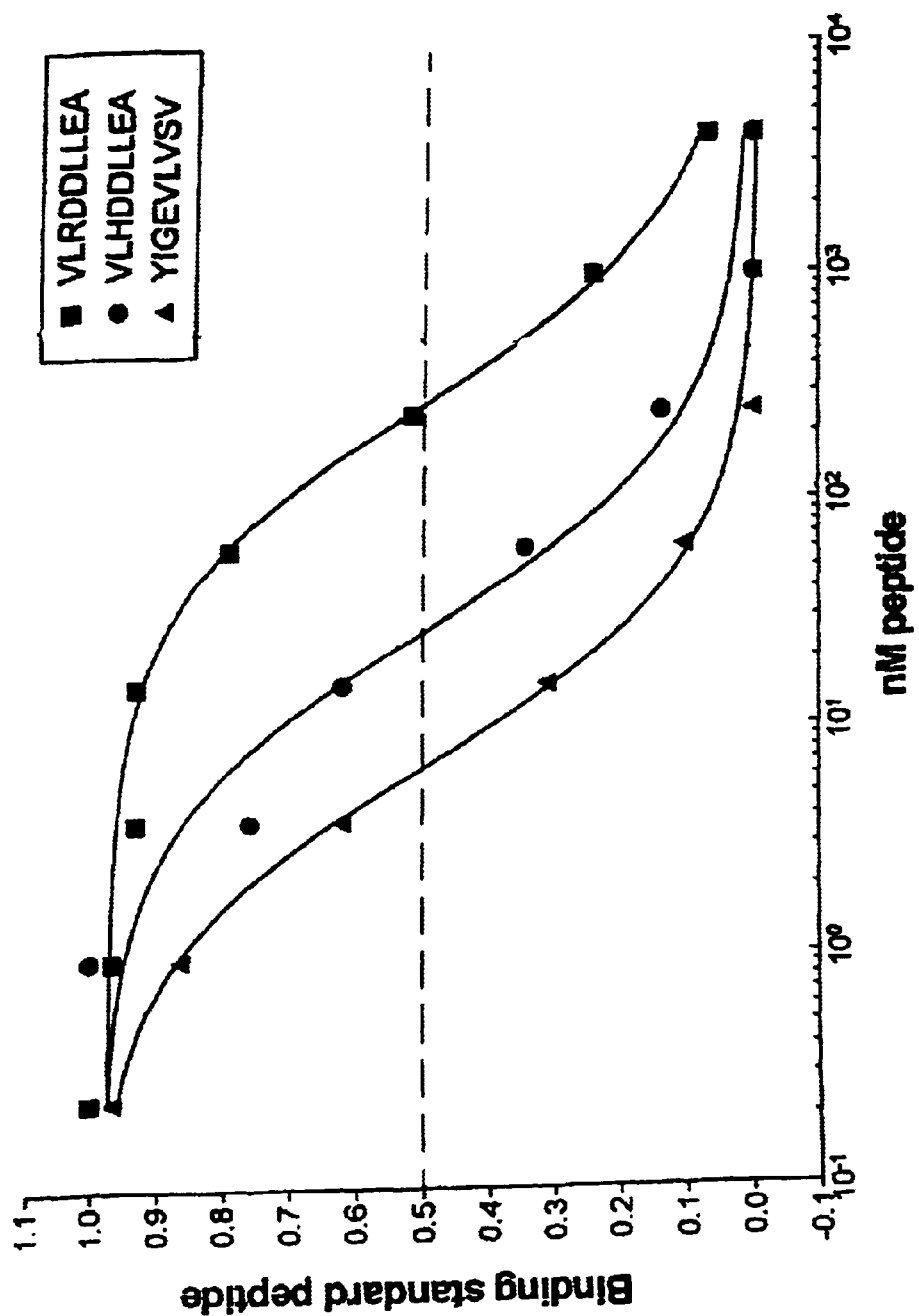
FIG. 4a. Binding of HA-1$^H$ and HA-1$^R$ peptides to HLA-A2.1. The binding of HA-1$^H$ and HA-1$^R$ peptides were assayed for their ability to inhibit the binding of fluorescent peptide FLPSDCFPSV (SEQ. I.D. NO. 17) to recombinant HLA-A2.1 and b2-microglobulin in a cell free peptide binding assay. One representative experiment is shown. The IC50 is determined on the results of 4 experiments and was 30 nM for VLHDDLLEA (SEQ. I.D. NO. 17) and 365 nM for VLRDDLLEA (SEQ. I.D. NO. 5) (FIG. 4b.) Reconstitution assay with different concentrations of synthetic HA-1$^R$ peptide with HA-1 specific T cells. The HA-1$^R$ peptide was titrated and preincubated with T2 cells. Three HA-1 specific T cell clones, 5W38, 3HA15 and clone 15 were added and a 4 hr $^{51}$Cr-release assay was performed. Background lysis of T2 by the CTL in the absence of any peptide was for 3HA15 4%, for clone 15 10% and for 5W38 2%. Positive control lysis was for 3HA15 46%, for clone 15 47% and 5W38 48%.
Figure 4B:
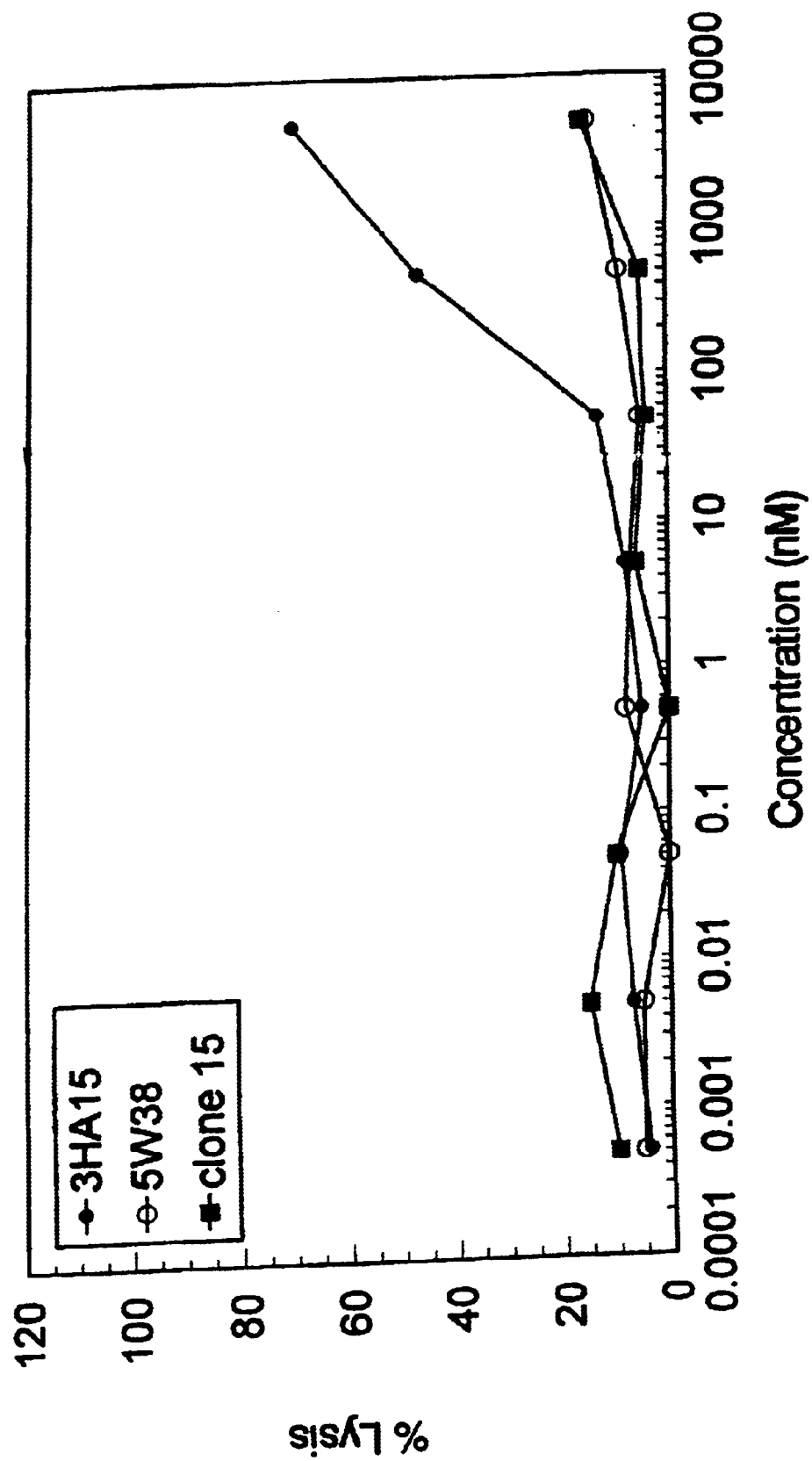
Figure 5:
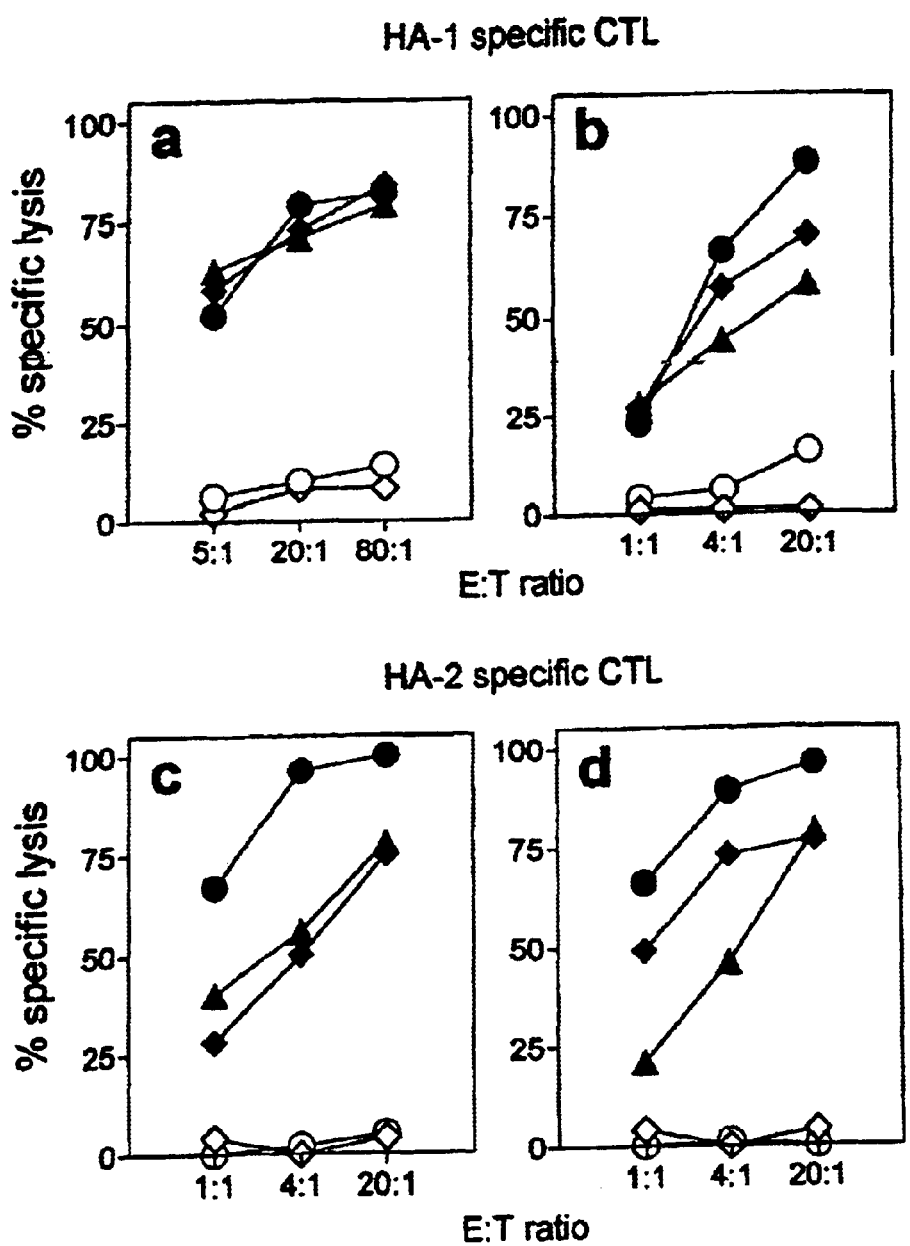
FIG. 5. Cytotoxic T cell activity against peptide pulsed and mHag positive target cells by two ex vivo induced HA-1 (a, b) and two ex vivo induced HA-2 specific CTLs (c, d). CTLs shown in a, c, d are induced using PBDC, whereas CTLs shown in b are induced using BMDC. Target cells: autologous PHA blasts (◊); autologous PHA blasts pulsed with peptide (♦); EBV-LCL positive for HA-1 (n=4) or HA-2 (n=3) (Δ); EBV-LCL negative for HA-1 (n=3) or HA-2 (n=3) (○); HA-1 or HA-2 negative EBV-LCL pulsed with HA-1 or HA-2 peptide(●).
Figure 6:
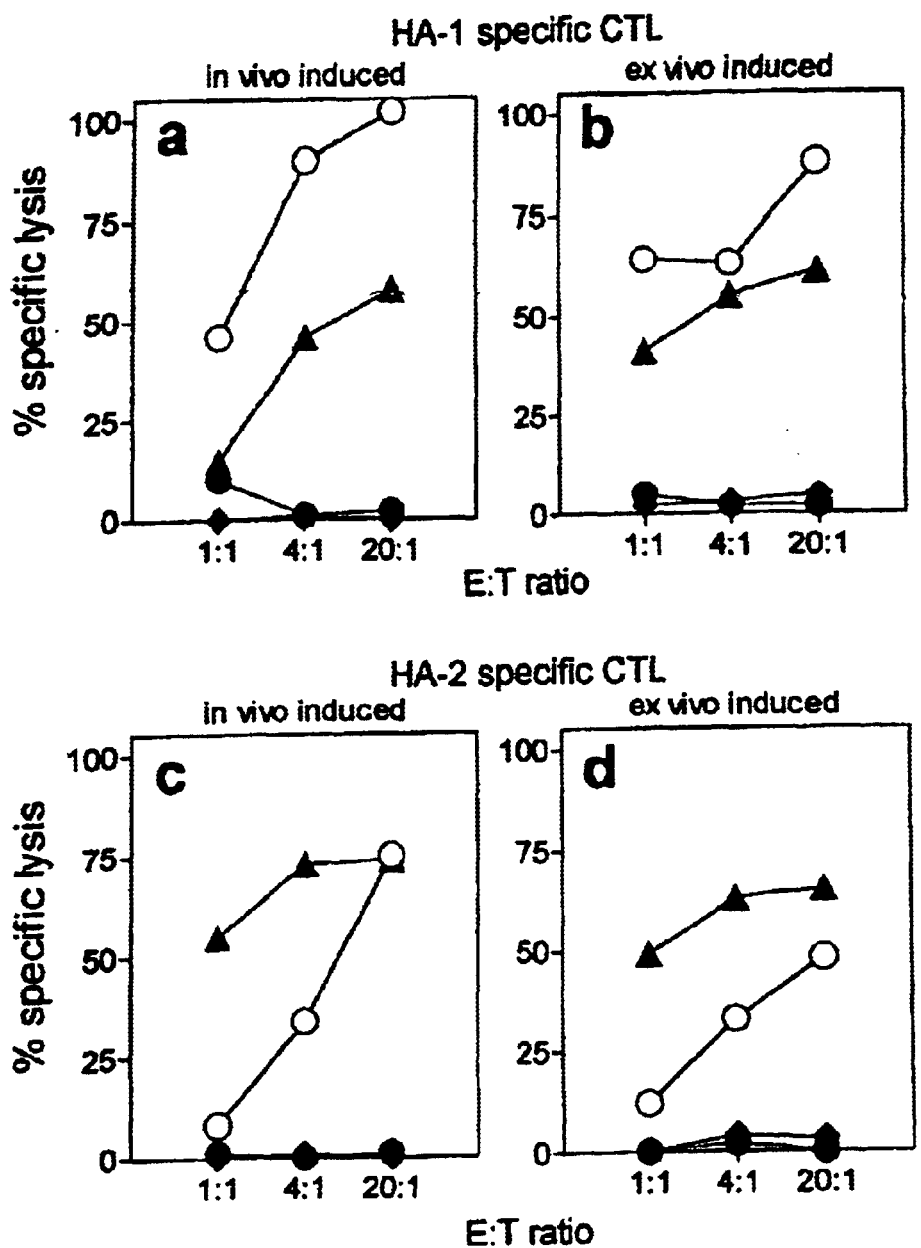
FIG. 6. Hematopoietic cell restricted cytolysis mediated by in vivo (a, c) and ex vivo (b, d) induced HA-1 (a, b) and HA-2 (c, d) specific CTLs. All target cells were derived from the same HLA-A2+, HA-1+, HA-2+ blood donor. Target cells: PHA blasts (Δ); fibroblasts (♦); Fibroblasts cultured with IFN-γ+ TNF-α (both 300 U/ml ) (●); Fibroblasts cultured with IFN-γ plus TNF-α and pulsed with 10 μg/ml peptide (○).
Figure 7:
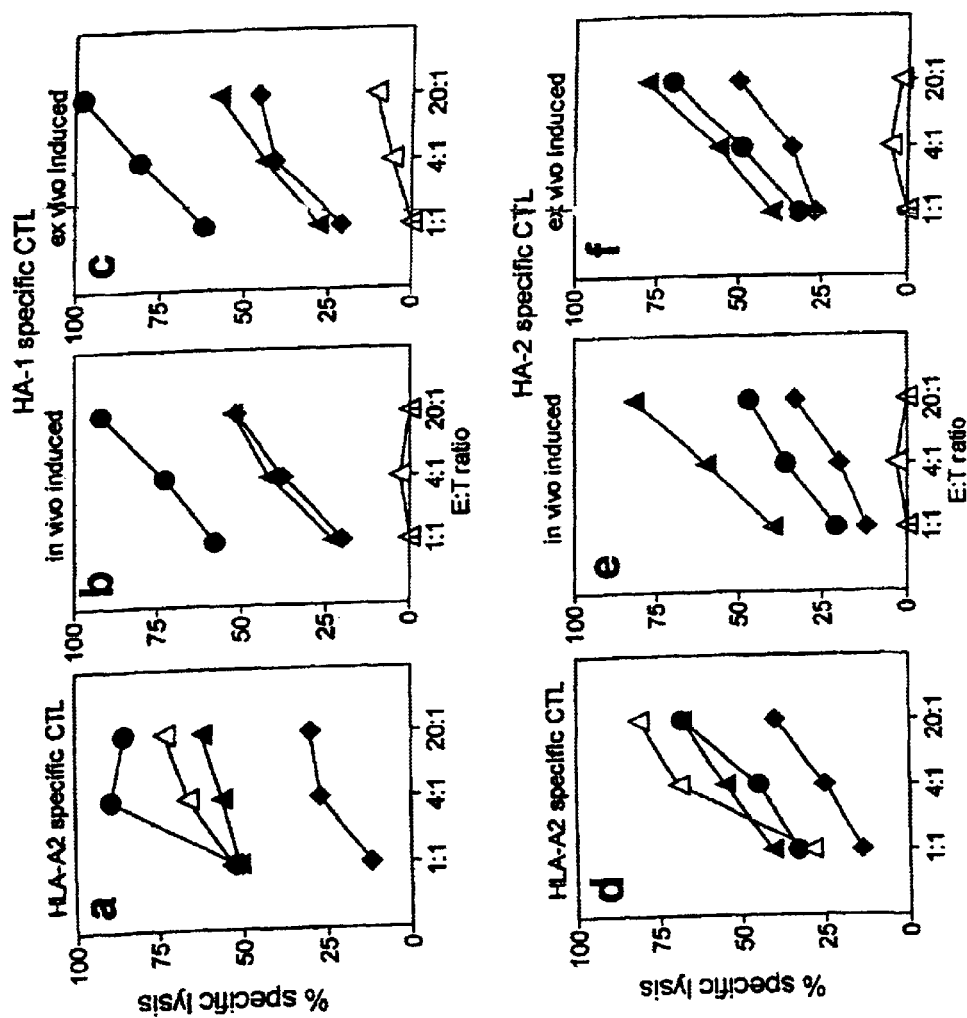
FIG. 7. Lysis of HA-1$^+$ (a, b, c) or HA-2$^+$ (d, e, f) positive leukemia cells by in vivo (b, c) and ex vivo (c, f) induced HA-1 and HA-2 specific CTLs. Lysis of target cells by control HLA-A2 specific CTL clone is shown in a and d. Target cells: HA-1 or HA-2 negative EBV-LCL (▢), HA-1 or HA-2 positive EBV-LCL (Δ), Leukemia cells positive for HA-1 (n=4) or HA-2 (n=3) (♦), HA-1 or HA-2 positive leukemic cells cultured with IFN-γ+ TNF-α (●).

1. Beatty, P. G. et al. Marrow transplantation from HLA-matched unrelated donors for treatment of hematological malignancies. *Transplantation* 51, 443–447 (1997).
2. Marks, D. I. et al Allogeneic bone marrow transplantation for chronic myeloid leukemia using sibling and volunteer unrelated donors. A comparison of complications in the first 2 years. *Ann. Intern. Med.* 119, 207–214 (1993).
3. Goulmy, F. et al. Mismatches of minor histocompatibility antigens between HLA.-identical donors and recipients and the development of graft-versus-host disease after bone marrow transplantation. *N. Engl. J. Med.* 334, 281–285 (1996).
4. den Haan, J. M. et al. Identification of a graft versus host disease-associated human minor histocompatibility antigen. *Science* 268, 1476–1480 (1995).
5. Wang, W. et al. Human H-Y: a male-specific histocompatibility antigen derived from the SMCY protein [see comments]. *Science* 269, 1588–1590 (1995).
6. Meadows, L. et al. The HLA-A*0201-restricted H-Y antigen contains a posttranslationally modified cysteine that significantly affects T cell recognition. *Immunity.* 6, 273–281 (1997).
7. van Els, C. A. et al. Immunogenetics of human minor histocompatibility antigens: their polymorphism and inmunodominance. *Immunogenetics* 35, 161–165 (1992).
8. de Bueger, M., Bakker, A., van Rood, J. J., Van der Woude, F. & Goulmy, E. Tissue distribution of human minor histocompatibility antigens. Ubiquitous versus restricted tissue distribution indicates heterogeneity among human cytotoxic T lymphocyte-defined non-MHC antigens. *J. Immunol.* 149, 1788–1794 (1992).
9. Van Lochem, E., van der Keur, M., Mommnaas, A. M., de Gast, G. C. & Goulmy, E. Functional expression of minor histocompatibility antigens on human peripheral blood dendritic cells and epidermal Langerhans cells. *Transpl. Immunol.* 4, 151–157 (1996).
10. van der Harst, D. et al. Recognition of minor histocompatiblity antigens on lymphocytic arid myeloid leukemic cells by cytotoxic T-cell clones. *Blood* 83, 1060–1066 (1994).
11. Schreuder, G. M. et al. A genetic analysis of human minor histocompatibility antigens demonstrates Mendelian segregation independent of HLA. *Immunogenetics* 38, 98–105 (1993).
12. Goulmy, E., Pool, J. & van den Elsen, P. J. Interindividual conservation of T-cell receptor beta chain variable regions by minor histocompatibility antigen-specific HLA-A*0201-restricted cytotoxic T-cell clones. *Blood* 85, 2478–2481 (1995).

13. Ruppert, J., Sidney, J., Celis, E., Kubo, R. T., Grey, H. M. & Sette, A. Prominent role of secondary anchor residues in peptide binding to HLA-A2.1 molecules. *Cell* 74, 929–937 (1993).
14. Chen, Y. et al. Naturally processed peptides longer than nine amino acid residues bind to the class I MHC molecule HLA-A2.1 with high affinity and in different conformations. *J. Immunol.* 152, 2874–2881 (1994).
15. Loveland, B., Wang, C. R., Yonekawa, H., Hennel, E. & Lindahl, K. F. Maternally transmitted histocompatibility antigen of mice: a hydrophobic peptide of a mitochondrially encoded protein. *Cell* 60, 971–980 (1990).
16. Loveland, B. E., Fischer Lindahl, K. The definition and expression of minor histocompatibility antigens. McCluskey J., editors Antigen processing and recognition. London: CRC Press, 9, 173–92 (1991).
17. Lindahl, K. F. Minor histocompatibility antigens. *Trends. Genet.* 7, 219–224 (1991).
18. Perreault, C., Jutras, J., Roy, D. C., Filep, J. G. & Brochu, S. Identification of an immunodominant mouse minor histocompatibility antigen (MiHA). T cell response to a single dominant MiHA causes graft-versus-host disease. *J. Clin. Invest.* 98, 622–628 (1996).
19. Morse, M. C. et al. The COI mitochondrial gene encodes a minor histocompatibility antigen presented by H2-M3. *J. Immunol.* 156, 3301–3307 (1996).
20. Scott, D. M. et al. Identification of a mouse male-specific transplantation antigen, H-Y. *Nature* 376, 695–698 (1995).
21. Greenfield, A. et al. An H-YDb epitope is encoded by a novel mouse Y chromosome gene. *Nat. Genet.* 14, 474–478 (1996).
22. Martin, P. J. Increased disparity for minor histocompatibility antigens as a potential cause of increased GvHD risk in marrow transplantation from unrelated donors compared with related donors. *Bone Marrow Transplant.* 8, 217–223 (1991).
23. Goulmy, E., Gratama, J. W., Blokland, E., Zwaan, F. E. & van Rood, J. J. A minor transplantation antigen detected by MHC-restricted cytotoxic T lymphocytes during graft-versus-host disease. *Nature* 302, 159–161 (1983).
24. de Bueger, M. et al. Isolation of an HLA-A2.1 extracted human minor histocompatibility peptide. *Eur. J. Immunol.* 23, 614–618 (1993).
25. Hunt, D. F. et al. Characterization of peptides bound to the class I MHC molecule HLA-A2.1 by mass spectrometry. *Science* 255, 1261–1263 (1992).
26. Ottenhoff, T. H. M., Geluk, A., Toebes, M., Benckhuijsen, W. E., van Meijgaarden, K. E. & Drijfhout, J. W. A sensitive fluorometric assay for quantitatively measuring specific peptide binding to HLA class I and class II molecules. *J. Immunol. Methods* 200, 89–97 (1997).
27. Tan, T. L. R., Geluk, A., Toebes, M., Ottenhoff, T. H. M. & Drijfhout, J. W. A novel, highly efficient peptide-HLA class I binding assay using unfolded heavy chain molecules; identification of HIV-1 derived peptides that bind to HLA-A*0201 and HLA-A*0301. *Submitted* (1997).
28. Traversari, C. et al. Transfection and expression of a gene coding for a human melanoma antigen recognized by autologous cytolytic T lymphocytes. *Immunogenetics* 35, 145–152 (1992).
29. O Reilly, R. J. Allogeneic bone marrow transplantation: Current status and future directions. *Blood* 62: 941–964 (1983).
30. Horowitz, M. M. et al. Graft-versus-leukemia reactions after bone marrow transplantation. *Blood* 75: 555–562. (1990).
31. Ringden, O. et.al. Allogeneic bone marrow transplantation for leukemia: factors of importance for long-term survival and relapse. *Bone Marrow Transplant* 3: 281–290. (1988).
32. Kolb, H. J. and Holler, E. Adoptive immunotherapy with donor lymphocyte transfusions. *Curr Opin Oncol* 9: 139–145. (1997).
33. Kolb, H. J. et.al. Graft-versus-leukemia effect of donor lymphocyte transfusions in marrow grafted patients. European Group for Blood and Marrow Transplantation Working Party Chronic Leukemia. *Blood* 86: 2041–2050. (1995).
34. Gratwohl, A. et.al. Acute graft-versus-host disease: grade and outcome in patients with chronic myelogenous leukemia Working Party Chronic Leukemia of the European Group for Blood and Marrow Transplantation. *Blood* 86: 813–818. (1995).
35. Goulmy, E. Human minor histocompatibility antigens: new concepts for marrow transplantation and adoptive immunotherapy. *Immunol Rev* 157: 125–140. (1997).
36. Niederwieser, D. et.al. Correlation of minor histocompatibility antigen-specific cytotoxic T lymphocytes with graft-versus-host disease status and analyses of tissue distribution of their target antigens. *Blood* 81: 2200–2208. (1993).
37. Faber, L. M. et.al. Recognition of clonogenic leukemic cells, remission bone marrow and HLA- identical donor bone marrow by CD8+ or CD4+ minor histocompatibility antigen-specific cytotoxic T lymphocytes. *J Clin Invest* 96: 877–883. (1995).
38. Falkenburg, J. H. F. et.al. Growth inhibition of clonogenic leukemic precursor cells by minor histocompatibility antigen-specific cytotoxic T lymphocytes. *J Exp Med* 174: 27–33. (1991).
39. den Haan, J. M. et. al. The minor histocompatibility antigen HA-1: a diallelic gene with a single amino acid polymorphism. *Science* 279: 1054–1057. (1998).
40. Banchereau, J. and Steinman, R. M. Dendritic cells and the control of immunity. *Nature* 392: 245–252. (1998).
41. Bonini, C. et.al. HSV-TK gene transfer into donor lymphocytes for control of allogeneic graft-versus-leukemia [see comments]. *Science* 276: 1719–1724. (1997).
42. Heslop, H. E. et.al. Long-term restoration of immunity against Epstein-Barr virus infection by adoptive transfer of gene-modified virus-specific T lymphocytes. *Nature Medicine* 2: 551–555. (1996).
43. van Lochem, E. G., Schreuder, G. M., Tilanus, M. G., de Gast, G. C., and Goulmy, E. Dendritic cells induce HLA-DP-specific T-cell proliferation between MLR-negative siblings. *Immunogenetics* 41: 134–138. (1995).

TABLE 1

| CELL | CTL analysis HA-1 phenotype | KIAA0223 sequence | SEQ ID NO | Nr. of clones sequenced | DNA analysis HA-1 phenotype |
|---|---|---|---|---|---|
| DH | HA-1-/- | GAGTGTGTGTTGCGTGACGACCTCCTTGAGGCCCGCCG | (SEQ ID NO:13) | (6/6 clones) | HA-1$^R$/HA-1$^R$ |
|  |  | E  C  V  L  R  D  D  L  L  E  A  R  R | (SEQ ID NO:14) |  |  |

TABLE 1-continued

| CELL | CTL analysis HA-1 phenotype | KIAA0223 sequence | SEQ ID NO | Nr. of clones sequenced | DNA analysis HA-1 phenotype |
|---|---|---|---|---|---|
| vR | HA-1+/+ | GAGTGTGTGCTGCATGACGACCTCCTTGAGGCCCGCCG | (SEQ ID NO:15) | (6/6 clones) | HA-1$^M$/HA-1$^H$ |
|  |  | E  C  V  L  H  D  D  L  L  E  A  R  R | (SEQ ID NO:16) |  |  |
| KG-1 | HA-1+ | OAGTGTGTGTTGCGTGAGGACCTCCTTGAGGCCCGCCG | (SEQ ID NO:13) | (1/8 clones) | HA-1$^R$/HA-1$^H$ |
|  |  | E  C  V  L  R  D  D  L  L  E  A  R  R | (SEQ ID NO:14) |  |  |
|  |  | GAGTGTGTGCTGCATGACGACCTCCTTGAGGCCCGCCG | (SEQ ID NO:15) | (7/8 clones) |  |
|  |  | E  C  V  L  H  D  D  L  L  E  A  R  R | (SEQ ID NO:16). |  |  |

What is claimed is:

1. A peptide consisting of the sequence VLXDDLLEA (SEQ ID NO:1), wherein X represents a histidine or an arginine residue.

2. The peptide of claim 1, wherein X is a histidine residue.

3. A preparation for stimulating the cytotoxic T lymphocytes (CTLs) comprising the peptide of claim 1.

4. The preparation for stimulating the cytotoxic T lymphocytes (CTLs) of claim 3, wherein X is a histidine residue.

5. A formulation comprising the peptide of claim 1.

6. The formulation of claim 5, wherein X is a histidine residue.

* * * * *

```
                              SEQUENCE LISTING

<160> NUMBER OF SEQ ID NOS: 17

<210> SEQ ID NO 1
<211> LENGTH: 9
<212> TYPE: PRT
<213> ORGANISM: Artificial sequence
<220> FEATURE:
<223> OTHER INFORMATION: obtained from histocompatibility antigen
<220> FEATURE:
<221> NAME/KEY: MISC_FEATURE
<222> LOCATION: (3)..(3)
<223> OTHER INFORMATION: Xaa is HISTIDINE OR ARGININE RESIDUE

<400> SEQUENCE: 1

Val Leu Xaa Asp Asp Leu Leu Glu Ala
1               5

<210> SEQ ID NO 2
<211> LENGTH: 9
<212> TYPE: PRT
<213> ORGANISM: Artificial sequence
<220> FEATURE:
<223> OTHER INFORMATION: obtained from histocompatibility antigen

<400> SEQUENCE: 2

Val Leu His Asp Asp Leu Leu Glu Ala
1               5

<210> SEQ ID NO 3
<211> LENGTH: 9
<212> TYPE: PRT
<213> ORGANISM: Artificial sequence
<220> FEATURE:
<223> OTHER INFORMATION: obtained from histocompatibility antigen
<220> FEATURE:
<221> NAME/KEY: MISC_FEATURE
<222> LOCATION: (2)..(2)
<223> OTHER INFORMATION: Xaa is ISOLEUCINE OR LEUCINE

<400> SEQUENCE: 3

Tyr Xaa Thr Asp Arg Val Met Thr Val
1               5

<210> SEQ ID NO 4
<211> LENGTH: 9
<212> TYPE: PRT
<213> ORGANISM: Artificial sequence
<220> FEATURE:
<223> OTHER INFORMATION: obtained from histocompatibility antigen
```

```
<220> FEATURE:
<221> NAME/KEY: MISC_FEATURE
<222> LOCATION: (2)..(7)
<223> OTHER INFORMATION: Xaa is LEUCINE OR ISOLEUCINE

<400> SEQUENCE: 4

Val Xaa His Asp Asp Xaa Xaa Glu Ala
1               5

<210> SEQ ID NO 5
<211> LENGTH: 9
<212> TYPE: PRT
<213> ORGANISM: Artificial sequence
<220> FEATURE:
<223> OTHER INFORMATION: obtained from KIAA0223 partial complementary
      DNA

<400> SEQUENCE: 5

Val Leu Arg Asp Asp Leu Leu Glu Ala
1               5

<210> SEQ ID NO 6
<211> LENGTH: 25
<212> TYPE: DNA
<213> ORGANISM: Artificial sequence
<220> FEATURE:
<223> OTHER INFORMATION: synthesized sequence, Reverse primer

<400> SEQUENCE: 6
gctcctgcat gacgctctgt ctgca                                       25

<210> SEQ ID NO 7
<211> LENGTH: 24
<212> TYPE: DNA
<213> ORGANISM: Artificial sequence
<220> FEATURE:
<223> OTHER INFORMATION: synthesized sequence, Forward primer

<400> SEQUENCE: 7
gacgtcgtcg aggacatctc ccat                                        24

<210> SEQ ID NO 8
<211> LENGTH: 25
<212> TYPE: DNA
<213> ORGANISM: Artificial sequence
<220> FEATURE:
<223> OTHER INFORMATION: synthesized sequence, Reverse Primer

<400> SEQUENCE: 8
gaaggccaca gcaatcgtct ccagg                                       25

<210> SEQ ID NO 9
<211> LENGTH: 30
<212> TYPE: DNA
<213> ORGANISM: Artificial sequence
<220> FEATURE:
<223> OTHER INFORMATION: synthesized sequence, HA-1" allele primer H1

<400> SEQUENCE: 9
ccttgagaaa cttaaggagt gtgtgctgca                                  30

<210> SEQ ID NO 10
<211> LENGTH: 30
<212> TYPE: DNA
<213> ORGANISM: Artificial sequence
<220> FEATURE:
<223> OTHER INFORMATION: synthesized sequence, HA-1r allele primer R1
```

-continued

```
<400> SEQUENCE: 10
ccttgagaaa cttaaggagt gtgtgttgcg                                        30

<210> SEQ ID NO 11
<211> LENGTH: 33
<212> TYPE: DNA
<213> ORGANISM: Artificial sequence
<220> FEATURE:
<223> OTHER INFORMATION: synthesized sequence, Forward KIAA00223 based
      PCR primer

<400> SEQUENCE: 11
ccggcatgga cgtcgtcgag gacatctccc atc                                    33

<210> SEQ ID NO 12
<211> LENGTH: 30
<212> TYPE: DNA
<213> ORGANISM: Artificial sequence
<220> FEATURE:
<223> OTHER INFORMATION: synthesized sequence, Reverse KIAA00223 based
      PCR primer

<400> SEQUENCE: 12
ctacttcagg ccacagcaat cgtctccagg                                        30

<210> SEQ ID NO 13
<211> LENGTH: 38
<212> TYPE: DNA
<213> ORGANISM: Artificial sequence
<220> FEATURE:
<223> OTHER INFORMATION: obtained from HA-1-/- phenotype

<400> SEQUENCE: 13
gagtgtgtgt tgcgtgacga cctccttgag gcccgccg                               38

<210> SEQ ID NO 14
<211> LENGTH: 13
<212> TYPE: PRT
<213> ORGANISM: Artificial sequence
<220> FEATURE:
<223> OTHER INFORMATION: obtained from HA-1-/- phenotype

<400> SEQUENCE: 14

Glu Cys Val Leu Arg Asp Asp Leu Leu Glu Ala Arg Arg
1               5                   10

<210> SEQ ID NO 15
<211> LENGTH: 38
<212> TYPE: DNA
<213> ORGANISM: Artificial sequence
<220> FEATURE:
<223> OTHER INFORMATION: obtained from HA-1+/+ phenotype

<400> SEQUENCE: 15
gagtgtgtgc tgcatgacga cctccttgag gcccgccg                               38

<210> SEQ ID NO 16
<211> LENGTH: 13
<212> TYPE: PRT
<213> ORGANISM: Artificial sequence
<220> FEATURE:
<223> OTHER INFORMATION: obtained from HA-1+/+ phenotype

<400> SEQUENCE: 16

Glu Cys Val Leu His Asp Asp Leu Leu Glu Ala Arg Arg
1               5                   10
```

```
<210> SEQ ID NO 17
<211> LENGTH: 10
<212> TYPE: PRT
<213> ORGANISM: Unknown
<220> FEATURE:
<223> OTHER INFORMATION: fluorescent peptide that can bind recombinant
      HLA-A2.1 and b2microglobulin
<400> SEQUENCE: 17

Phe Leu Pro Ser Asp Cys Phe Pro Ser Val
1               5                   10
```